United States Patent
Hechler et al.

(10) Patent No.: US 11,976,131 B2
(45) Date of Patent: May 7, 2024

(54) HUMANIZED ANTIBODIES AGAINST PSMA

(71) Applicant: Heidelberg Pharma Research GmbH, Ladenburg (DE)

(72) Inventors: Torsten Hechler, Ladenburg (DE); Andreas Pahl, Ladenburg (DE)

(73) Assignee: Heidelberg Pharma Research GmbH, Ladenburg (DE)

( * ) Notice: Subject to any disclaimer, the term of this patent is extended or adjusted under 35 U.S.C. 154(b) by 560 days.

(21) Appl. No.: 17/264,209

(22) PCT Filed: Jul. 30, 2019

(86) PCT No.: PCT/EP2019/070407
§ 371 (c)(1),
(2) Date: Jan. 28, 2021

(87) PCT Pub. No.: WO2020/025564
PCT Pub. Date: Feb. 6, 2020

(65) Prior Publication Data
US 2023/0250189 A1     Aug. 10, 2023

(30) Foreign Application Priority Data

Jul. 31, 2018   (EP) ..................... 18186591

(51) Int. Cl.
*A61P 35/00*    (2006.01)
*C07K 16/30*    (2006.01)

(52) U.S. Cl.
CPC .......... *C07K 16/3069* (2013.01); *A61P 35/00* (2018.01); *C07K 2317/24* (2013.01); *C07K 2317/41* (2013.01); *C07K 2317/565* (2013.01); *C07K 2317/622* (2013.01); *C07K 2317/92* (2013.01)

(58) Field of Classification Search
CPC ................................................. C07K 16/3069
USPC ..................................................... 424/133.1
See application file for complete search history.

(56) References Cited

U.S. PATENT DOCUMENTS

2006/0088539 A1    4/2006 Bander

FOREIGN PATENT DOCUMENTS

| WO | WO 2006/125481 A1 | 11/2006 |
| WO | WO 2010/037836 A2 | 4/2010 |
| WO | WO 2011/121110 A1 | 10/2011 |
| WO | WO 2020/002015 A1 * | 1/2020 |

OTHER PUBLICATIONS

Zhang et al (Advanced Healthcare Materials, 2(5): 625-763).*
Bander et al. "Targeted Systemic Therapy of Prostate Cancer With a Monoclonal Antibody to Prostate-Specific Membrane Antigen," *Seminars in Oncology*, 30(5): 667-677 (2003).
Behe et al., "In Vivo Testing of $^{177}$Lu-Labelled Anti-PSMA Antibody as a New Radioimmunotherapeutic Agent Against Prostate Cancer," In Vivo, 25(1): 55-59 (2011).
De Groot et al., "Beyond humanization and de-immunization: tolerization as a method for reducing the immunogenicity of biologics," *Expert Review of Clinical Pharmacology*, 6(6): 651-662 (2013).
Lütje et al., "PSMA ligands in prostate cancer—Probe optimization and theranostic applications," *Methods*, 130: 42-50 (2017).
Nováková et al. "Novel Monoclonal Antibodies Recognizing Human Prostate-Specific Membrane Antigen (PSMA) as Research and Theranostic Tools," *The Prostate*, 77(7): 749-764 (2017).
Parker et al., "Design, production, and characterization of a single-chain variable fragment (ScFv) derived from the prostate specific membrane antigen (PSMA) monoclonal antibody J591," *Protein Expression and Purification*, 89(2): 136-145 (2013).
Stallwood et al., "Antibody Humanization and De-immunization," *Lonza* (2011) [retrieved from the Internet: URL:https://www.google.com/search?q=yvette+stallwood+antibody+humanization+and+deimmunization+&ie=utf-8&oe=utf-8].
Wolf et al. "Preclinical Evaluation of a Recombinant Anti-Prostate Specific Membrane Antigen Single-Chain Immunotoxin Against Prostate Cancer," *J. Immunother.*, 33(3): 262-271 (2010).
Wolf, et al. "Three Conformational Antibodies Specific for Different PSMA Epitopes Are Promising Diagnostic and Therapeutic Tools for Prostate Cancer," *The Prostate*, 70(5): 562-569 (2010).
Colombian Patent Office, Office Action and Search Report in Colombian Patent Application No. NC2021/0000386 (dated Jan. 13, 2022).
European Patent Office, International Search Report in International Patent Application No. PCT/EP2019/070407 (dated Oct. 1, 2019).
European Patent Office, Communication Pursuant to Article 94(3) EPC in European Patent Application No. 19745146.1 (dated Mar. 2, 2022).
Japan Patent Office, Notice of Reasons for Rejection in Japanese Patent Application No. 2021-505326 (dated Mar. 14, 2023).
Japan Patent Office, Office Action in Japanese Patent Application No. 2021-505326 (dated Nov. 21, 2023).

* cited by examiner

*Primary Examiner* — Sean E Aeder
(74) *Attorney, Agent, or Firm* — Leydig, Voit & Mayer, Ltd.

(57) ABSTRACT

The present application relates to humanized and/or deimmunized antibodies, antibody fragments or antibody derivatives that bind to Prostate Specific Membrane Antigen (PSMA) and methods for using said antibodies, antibody fragments or antibody derivatives in the treatment of prostate cancer and other neoplastic as well as neurological diseases.

20 Claims, 7 Drawing Sheets
Specification includes a Sequence Listing.

|  | CDR H1 | CDR H2 |
| --- | --- | --- |
| 3F11-VH-1 | QVQLVQSGAEVKKPGASVKVSCKASGYTFTTYDINWLRQAPGQGLEWM | TISPGDGNTNYNENFKGRV |
| 3F11-VH-2 | QVQLVQSGAEVKKPGASVKVSCKASGYTFTTYDINWLRQAPGQGLEWM | TISPGDGNTNYAQKFQGRV |
| 3F11-VH-3 | QVQLVQSGAEVKKPGASVKVSCKASGYTFTTYDINWLRQAPGQGLEWM | TISPGDGNVNYAQKFQGRV |
| 3F11-VH-4 | QVQLVQSGAEVKKPGASVKVSCKASGYTFTTYDINWLRQAPGQGLEWM | TISPGDSVNYAQKFQGRV |

|  |  | CDR H3 |
| --- | --- | --- |
| 3F11-VH-1 | TLTIDKSTSTAYMELSSLRSEDTAVYYCAR | DGNFPYYAMDWGQGTLVTVSS |
| 3F11-VH-2 | TLTITSTSTAYMELSSLRSEDTAVYYCAR | DGNFPYYAMDWGQGTLVTVSS |
| 3F11-VH-3 | TLTITSTSTAYMELSSLRSEDTAVYYCAR | DGNFPYYAMDWGQGTLVTVSS |
| 3F11-VH-4 | TLTITSTSTAYMELSSLRSEDTAVYYCAR | DGNFPYYAMDWGQGTLVTVSS |

FIG. 3

HUMANIZED ANTIBODIES AGAINST PSMA

CROSS-REFERENCE TO RELATED APPLICATIONS

This patent application is the U.S. national phase of International Patent Application No. PCT/EP2019/070407, filed on Jul. 30, 2019, which claims the benefit of European Patent Application No. 18186591.6, filed on Jul. 31, 2018, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 44,489 bytes ASCII (Text) file named "751966ReplacementSequenceListing.txt," created Aug. 17, 2021.

FIELD OF THE INVENTION

The present application relates to humanized and/or deimmunized antibodies, antibody fragments or antibody derivatives that bind to Prostate Specific Membrane Antigen (PSMA) and methods for using said antibodies, antibody fragments or antibody derivatives in the treatment of prostate cancer and other neoplastic as well as neurological diseases.

BACKGROUND

The Prostate specific membrane antigen (PSMA), which is also known as glutamate carboxypeptidase II (GCPII), N-acetyl-L-aspartyl-L-glutamate peptidase I (NAALADase I) or N-acetyl-aspartylglutamate (NAAG) peptidase, is an enzyme that is encoded by the human folate hydrolase (FOLH1) gene. PSMA is a membrane-bound cell surface peptidase that plays different physiological roles and is expressed in various tissues such as the prostate, kidney, small intestine, central and peripheral nervous system. It is highly expressed by malignant prostate epithelial cells and vascular endothelial cells of numerous solid tumor malignancies, including glioblastomas, breast and bladder cancers. The protein is also involved in a variety of neurological diseases including schizophrenia and ALS.

PSMA is a class II transmembrane glycoprotein with a short N-terminal cytoplasmic tail of 18 amino acids (aa 1-18), a single membrane-spanning helix (aa 19-43), and an extracellular moiety consisting of aa 44-750 with an approximate molecular weight of 84 kDa (Barinka et al., 2004). The short N-terminal cytoplasmic tail has been shown to interact with membrane scaffold proteins that govern the endocytosis of some of the PSMA-bound substrates, such as clathrin, clathrin adaptor protein 2, filamin A (FLNa), and caveolin-1. The extracellular part is further divided in three domains: the protease (aa 57-116 and aa 352-590), the apical part (aa 117-351), and the C-terminal or dimerization domain (aa 591-750); these moieties collectively perform the substrate/ligand recognition role (Bařinka et al., 2012) (FIG. 1). With regard to aa sequence and domain organization, the 3-dimensional extracellular structure of PSMA resembles the transferrin receptor (Tfr). PSMA is enzymatically active only in its dimeric form. Dimerization as well as glycosylation are essential for the correct conformation and enzymatic activity of the molecule.

PSMA expression and localization in the normal human prostate are associated with the cytoplasm and apical side of the epithelium surrounding the prostatic ducts. Dysplastic and neoplastic transformation of prostate tissue results in the transfer of PSMA from the apical membrane to the luminal surface of the ducts. Although PSMA was originally thought to be prostate-specific, more recent studies have shown that it is also expressed by small intestine epithelial (brush-border) cells, proximal renal tubule cells and salivary glands as well as in the nervous system.

In the small intestine, PSMA is located in the brush border of the proximal jejunum, where it acts as a hydrolase on poly-γ-glutamated folate and actively transports the monoglutamylated folates into the blood stream (Navrátil et al., 2014). It thus exhibits both hydrolysing and endocytic functions, at least in humans and pigs. The endocytic internalization occurs through clathrin coated pits via receptor-mediated endocytosis. In the nervous system, PSMA, also termed as NAAG-Hydrolase, catalyses the hydrolysis of NAAG, which is a widely distributed neurotransmitter in the mammalian brain, to glutamate and N-acetylaspartate (NAA). The different roles of PSMA in different tissues have triggered broad exploration of various therapeutic approaches to target the delivery of drugs and small molecules specifically to PSMA-expressing cells (Evans et al., 2016).

PSMA expression levels are higher in the malignant tissues of different origin than in the normal and healthy tissues (Evans et al., 2016; Haffner et al., 2009). This expression pattern directly implies a role of PSMA in cancer progression and invasion and makes the molecule a desirable target for diagnosis and treatment of solid tumours.

For several reasons, PSMA is an ideal target in prostate cancer. First, it is significantly overexpressed on nearly all prostate cancer cells. The level of expression on prostate cancer cells is 100- to 1,000-fold higher than in normal tissue. PSMA is expressed in almost all prostate cancers; only 5%-10% of primary prostate cancer or prostate cancer lesions had negative PSMA results on PET (Eiber et al., 2017).

Second, its expression is further increased in advanced stages, in high grade metastatic disease, in hormone-refractory prostate cancer and in metastatic castration-resistant prostate cancer (mCRPC).

Third, in contrast to other prostate related antigens such as PSA, prostatic acid phosphatase and prostate secretory protein, PSMA as a type II integral membrane cell surface protein is not secreted and, therefore, is an excellent target for, e.g., antibody or other ligand-mediated therapy. After binding to the active center of the extracellular domain, PSMA ligands are internalized. Subsequent endosomal recycling increases the deposition, leading to enhanced tumor uptake, retention, and subsequent high local dose for therapeutic applications.

In general, prostate cancer metastases frequently involve the bone marrow and lymph nodes, which are locations that take up high levels of circulating antibodies and have been well responsive to monoclonal antibody therapies in other tumor types such as lymphoma and breast cancer (Nanus et al., 2003).

In prostate cancer, the expression of PSMA is negatively regulated by androgens (Israeli et al., 1993). Gene transcription analysis demonstrated that androgen can suppress the promoter of the PSMA gene. Therefore, the initiation of androgen deprivation therapy induces early but temporary upregulation of PSMA expression, downregulation under prolonged androgen deprivation therapy and, finally, overexpression of PSMA in androgen-resistant tumors. These effects could potentially be leveraged for improved therapy and diagnosis (Eiber et al., 2017). Albeit the direct role of PSMA in prostate cancer metastasis is still not fully understood, hormonal androgen ablation therapy on androgen sensitive cells has been shown to increase PSMA levels, and the increased expression of PSMA made the cells less invasive. PSMA knockdown, on the other hand, resulted in a fivefold increase in invasive activity.

Cancer of the prostate is the most commonly diagnosed cancer in men and the second most common cause of death in the Western civilization. Because of the significant mortality and morbidity associated with disease progression, there is an urgent need for new targeted treatments. There are various approaches presently being assessed for the treatment of prostate cancer. Small molecules, aptamers or antibodies are being used as specific ligands to exploit PSMA for targeted delivery of chemotherapeutic drugs (see Evans et al., 2016, for review). PSMA-targeted gene therapy approaches based on, e.g., RNAi, antisense RNA or aptamers as well as PSMA-mediated suicide gene therapy is currently under evaluation. In radioimmunotherapy which is presently being used in approximately 25% of patients with localized disease in prostate cancer (Cooperberg et al., 2010), the addition of a targeting ligand, such as a monoclonal antibody or aptamer, to a radionuclide allows for the targeting of a cancer-associated cell-surface antigen like PSMA and thus reduction of unwanted side effects and dosage enhancement. Immunotherapies based on primed dendritic cells (DC) or T-cells bearing a chimeric antigen receptor (CAR) against PSMA to elicit CTL activity against PSMA-positive tumour cells are at clinical stage.

Antibodies which bind PSMA have been described in the prior art. PSMA was first characterized by the murine monoclonal antibody 7E11, derived from mice immunized with partially purified cell membrane fractions, isolated from the human prostate adenocarcinoma (LNCap) cell line (Horoszewicz et al., 1986). This first published monoclonal antibody against PSMA recognizes the N-terminal end (MWNLLH) of the intracellular domain of PSMA (Troyer et al., 1995).

Four murine IgG monoclonal antibodies (J591, J415, J533 and E99) to the extracellular domain of PSMA have been prepared which, in contrast to 7E11, recognize two distinct non-competing epitopes located on the exterior of the cell (Liu et al., 1997; Nanus et al., 2003).

Wolf et al. (2010a) generated three different mouse anti-PSMA monoclonal antibodies 3/A12, 3/E7, and 3/F11 showing a strong binding to PSMA-positive prostate cancer LNCaP sub-cell line C4-2 with mean half-maximal saturation concentrations of between 9 and 17 nM (EP 1883698 B2). The antibodies stained epithelial cells on all normal and tumorous prostate tissue specimens tested. As revealed in competitive binding studies, the three monoclonal antibodies are binding to different extracellular PSMA epitopes. The epitope of 3/A12 was found to be close or partially overlapping with that of antibody J591.

An anti-PSMA single-chain antibody fragment (scFv), called D7, isolated by phage display from the monoclonal antibody 3/F11, was used for construction of an immunotoxin by C-terminal ligation of the *Pseudomonas* Exotoxin A to the cDNA of D7; this immunotoxin inhibited PSMA-positive prostate cancer cell growth in vitro as well as in vivo (Wolf et al., 2010b).

In contrast to the results obtained with monoclonal antibodies 3/A12, 3/E7, and 3/F11 which were derived from mice immunized with unpurified LNCaP cell lysate, the same researchers obtained three monoclonal antibodies K7, K12, and D20 from mice immunized with purified PSMA, which were highly reactive only with the isolated antigen, but showed weak or no reaction with viable LNCaP cells (Elsässer-Beile et al., 2006).

Thirteen different PSMA-specific mouse monoclonal antibodies were characterized in terms of their binding activity to native and denatured antigen by Tykvart et al. (2014).

WO2001009192 (Medarex) describes the development of human monoclonal antibodies to prostate-specific membrane antigen. Human anti-PSMA monoclonal antibodies were generated by immunizing mice with purified PSMA or enriched preparations of PSMA antigen. Such purified antigen is a denatured PSMA since it has been purified by immunoadsorption after cell lysis with ionic detergents.

WO1997035616 (Pacific Northwest Cancer Foundation) describes monoclonal antibodies specific for the extracellular domain of prostate-specific membrane antigen. Immunizations were performed with a C-terminal peptide or a PSMA-expressing tumor membrane preparation. The monoclonal antibodies obtained did not bind specifically to PSMA-expressing cells and can therefore not be used for diagnostic or therapeutic purposes.

Bander et al. (2003) disclosed monoclonal antibodies directed against prostate-specific membrane antigen. Since the immunization was performed with purified antigen, the monoclonal antibodies were not suited for cell binding, and no scFv could be obtained from any of these monoclonal antibodies. In WO1998/03873, describing the same antibodies or binding portions thereof which recognize an extracellular domain of prostate-specific membrane antigen, it could not be shown that the binding portions of the antibodies do in fact bind to the antigen.

Immunogenicity is a critical concern when developing an antibody-based drug (Almagro and Fransson, 2008). All exogenous proteins used for therapeutic purposes pose the risk of causing anti-drug antibody formation in recipients (Schellekens 2002), and the use of therapeutic proteins and antibodies of non-human origin has routinely been found to be associated with generation of anti-drug antibodies, often leading to formation of deleterious immune complexes and/or neutralization of the therapeutic agents. In addition to the origin and nature of the antibody, other factors have been shown to influence the immunogenicity such as the type of disease, route of administration and genetic background of recipients.

Thus, for various reasons, anti-PSMA antibodies described above from the prior art have not been suited for human therapy, in particular because of their immunogenic potential, lack of target recognition or insufficient binding affinity.

SUMMARY OF THE INVENTION

In view of the prior art, it was hence one object of the present invention to provide humanized antibodies, antibody fragments or antibody derivatives that bind prostate-specific membrane antigen (PSMA) with high affinity, in particular an epitope of the extracellular domain of PSMA, as described in the present application.

The antibodies, the antibody fragments or antibody derivatives thereof, disclosed herein comprise humanized sequences, in particular of the preferred VH- and VL-based antigen-binding region which maintain appropriate ligand affinity. The amino acid sequence modifications to obtain said humanized sequences may occur in the CDR regions and/or in the framework regions of the original antibody and/or in antibody constant region sequences.

It was one further object of the present invention to provide antibodies that specifically bind to native cell-surface PSMA and therefore have value in diagnostic and therapeutic applications focusing on PSMA as a target antigen for prostate cancer.

It was one further object of the present invention to provide compounds for use in methods for treatment of prostate cancer or neurologic disorders.

It was one further object of the present invention to provide compounds destroying prostate cancer cells expressing PSMA.

It was another object of the present invention to provide an antibody, antibody fragment or antibody derivative thereof, with a low or no immunogenicity in humans. Preferably this antibody is a monoclonal antibody, antibody fragment or antibody derivative thereof.

It was another object of the present invention to provide antibody-drug conjugates (ADCs) for use in methods of treatment of prostate cancer and other diseases, preferably comprising an amatoxin.

It was entirely surprising that the humanized sequences according to the present invention, in particular the CDR sequences of the VH and VL regions involved in binding to the target molecule, exhibit the specific and strong binding as demonstrated in the examples, and retain or even exceed the binding characteristics of the original murine antibody 3F11, without any affinity maturation which is usually required after humanization of antibodies. A skilled person would not have expected that the binding characteristics of the humanized variants would be similar to, not to speak of even better binding characteristics than the original murine antibody. Considering the sequence changes in the variable domains, and in particular the CDRs, the beneficial binding characteristics of the humanized sequences demonstrated herein must be considered a surprising technical effect.

It was, furthermore, completely surprising that with the humanized sequences according to the present invention, when expressed in eukaryotic host cells, significantly better expression yields were obtained than with the parental antibody sequences. Biotechnological production of humanized antibodies, or antibody fragments or antibody derivatives thereof, according to the present invention thus can be performed at considerably lower cost than with the parental antibody sequences.

These and further objects are met with methods and means according to the independent claims of the present invention. The dependent claims are related to specific embodiments.

The invention and general advantages of its features will be discussed in detail below.

DESCRIPTION OF THE FIGURES

FIG. 3. Sequence alignment of variable heavy chain ($V_H$) regions of humanized/deimmunized variants of antibody 3F11. Amino acid substitutions versus murine 3F11-wt are in bold.

DETAILED DESCRIPTION OF THE INVENTION

Figure 1:
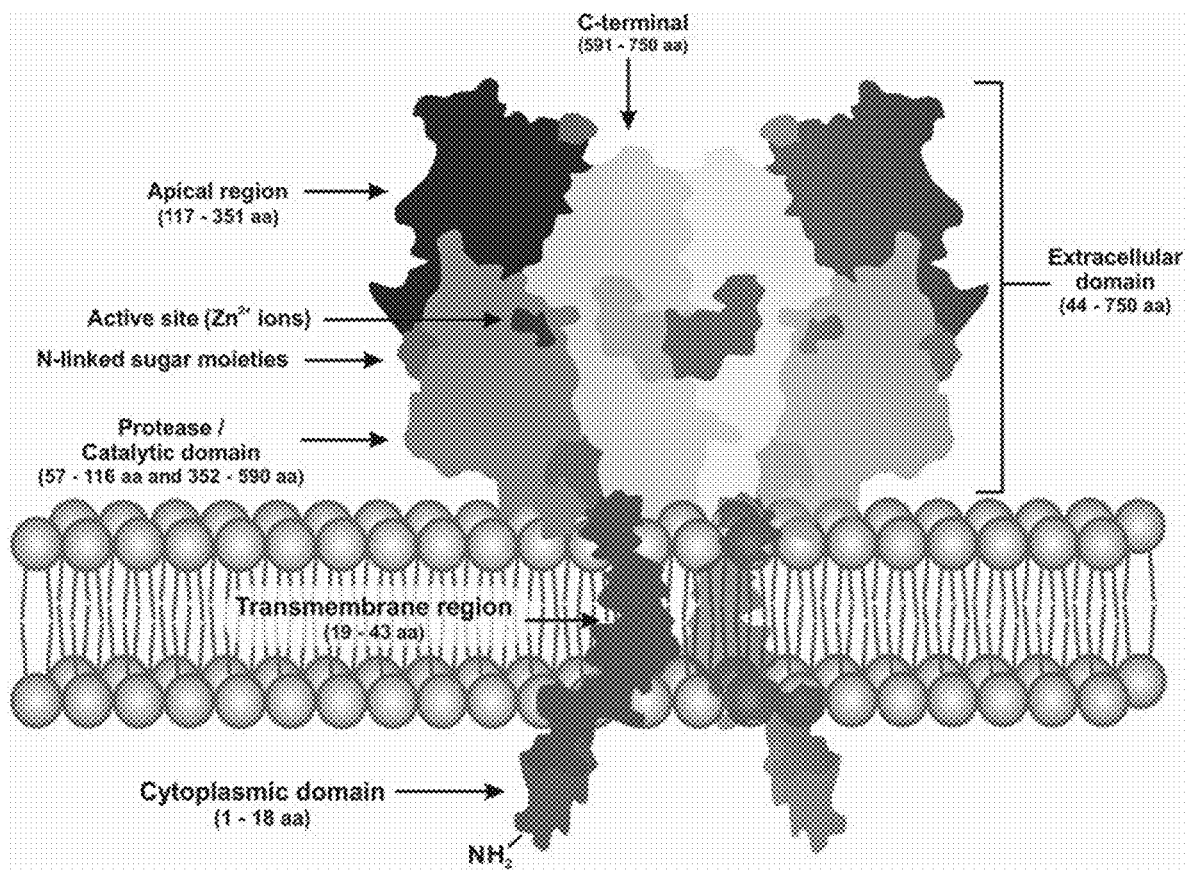
FIG. 1. Schematic representation of PSMA transmembrane protein as a homodimer (from Evans et al., 2016).
Figure 2:
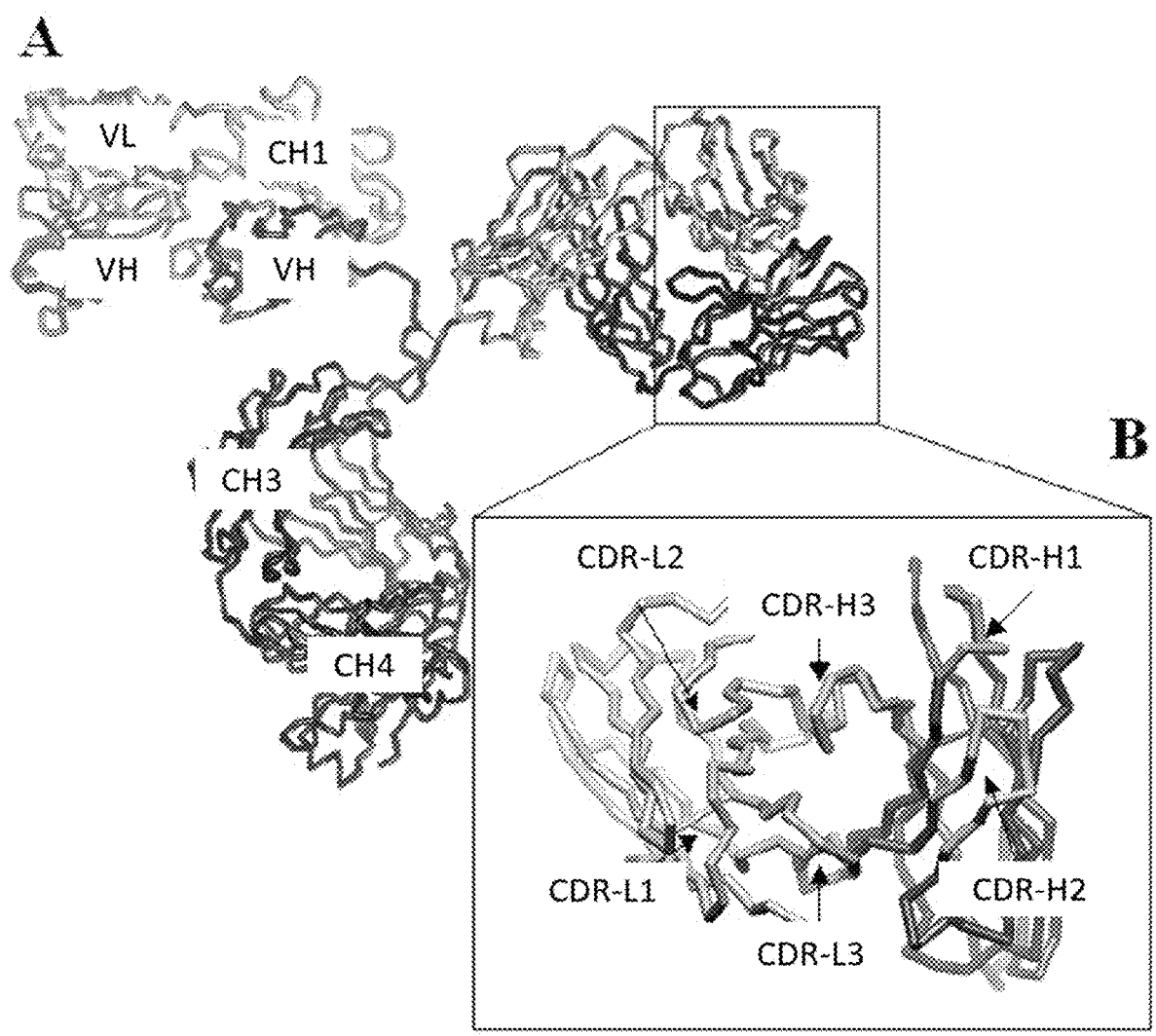
FIG. 2. Schematic representation of an antibody. IgG structure showing two identical heavy (H) chains and two identical light (L) chains. H chains have four domains, three C domains ($C_H1$ to $C_H3$) and one $V_H$. L chains have one CL domain and one $V_L$ domain. The Fv fragment (indicated by the square) is the portion of the molecule that interacts with the antigen. It is composed by non-covalent pairing of $V_L$ and $V_H$. The Fv fragment is shown from the antigen view indicating the placement of the hypervariable loops (from Almagro and Fransson, 2008).

Before the invention is described in detail, it is to be understood that this invention is not limited to the particular component parts of the devices described or process steps of the methods described as such devices and methods may vary. It is also to be understood that the terminology used herein is for purposes of describing particular embodiments only and is not intended to be limiting. It must be noted that, as used in the specification and the appended claims, the singular forms "a", "an", and "the" include singular and/or plural referents unless the context clearly dictates otherwise. It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

Furthermore, the content of the prior art documents referred to herein is incorporated by reference. This refers, particularly, for prior art documents that disclose standard or routine methods. In that case, the incorporation by reference has mainly the purpose to provide sufficient enabling disclosure and avoid lengthy repetitions.

As used herein, the term "antibody" shall refer to a protein consisting of one or more polypeptide chains encoded by immunoglobulin genes or fragments of immunoglobulin genes or cDNAs derived from the same. Said immunoglobulin genes include the light chain kappa, lambda and heavy chain alpha, delta, epsilon, gamma and mu constant region genes as well as any of the many different variable region genes.

The basic immunoglobulin (antibody) structural unit is usually a tetramer composed of two identical pairs of polypeptide chains, the light chains (L, having a molecular weight of about 25 kDa) and the heavy chains (H, having a molecular weight of about 50-70 kDa). Each heavy chain is comprised of a heavy chain variable region (abbreviated as VH or $V_H$) and a heavy chain constant region (abbreviated as CH or $C_H$). The heavy chain constant region is comprised of three domains, namely CH1, CH2 and CH3. Each light chain contains a light chain variable region (abbreviated as VL or $V_L$) and a light chain constant region (abbreviated as CL or $C_L$). The VH and $V_L$ regions can be further subdivided into regions of hypervariability, which are also called complementarity determining regions (CDR) interspersed with regions that are more conserved called framework regions (FR). Each VH and $V_L$ region is composed of three CDRs and four FRs arranged from the amino terminus to the carboxy terminus in the order of FR1, CDR1, FR2, CDR2, FR3, CDR3, FR4. The variable regions of the heavy and light chains form a binding domain that interacts with an antigen.

The CDRs are most important for binding of the antibody or the antigen binding portion thereof. The FRs can be replaced by other sequences, provided the three-dimensional structure which is required for binding of the antigen is retained. Structural changes of the construct most often lead to a loss of sufficient binding to the antigen.

The term "antigen binding portion" of the (monoclonal) antibody refers to one or more fragments of an antibody which retain the ability to specifically bind to the prostate specific membrane antigen in its native form. Examples of antigen binding portions of the antibody include a Fab fragment, a monovalent fragment consisting of the VL, VH, CL and CH1 domains, an F(ab')2 fragment, a bivalent fragment comprising two Fab fragments linked by a disulfid bridge at the hinge region, an Fd fragment consisting of the VH and CH1 domain, an Fv fragment consisting of the VL and VH domains of a single arm of an antibody, and a dAb fragment which consists of a VH domain and an isolated complementarity determining region (CDR).

As used herein, the term "monoclonal antibody (mAb)" shall refer to an antibody composition having a homogenous antibody population, i.e., a homogeneous population consisting of a whole immunoglobulin, or a fragment or derivative thereof. Particularly preferred, such antibody is selected from the group consisting of IgG, IgD, IgE, IgA and/or IgM, or a fragment or derivative thereof.

As used herein, the term "fragment" shall refer to fragments of such antibody retaining target binding capacities, e.g., a CDR (complementarity determining region), a hypervariable region, a variable domain (Fv), an IgG heavy chain (consisting of VH, CH1, hinge, CH2 and CH3 regions), an IgG light chain (consisting of VL and CL regions), and/or a Fab and/or F(ab)$_2$.

As used herein, the term "derivative" shall refer to protein constructs being structurally different from, but still having some structural relationship to, the common antibody concept, e.g., scFv, Fab and/or F(ab)$_2$, as well as bi-, tri- or higher specific antibody constructs. All these items are explained below.

Other antibody derivatives known to the skilled person are Diabodies, Camelid Antibodies, Domain Antibodies, bivalent homodimers with two chains consisting of scFvs, IgAs (two IgG structures joined by a J chain and a secretory component), shark antibodies, antibodies consisting of new world primate framework plus non-new world primate CDR, dimerised constructs comprising CH3+VL+VH, other scaffold protein formats comprising CDRs, and antibody conjugates (e.g., antibody, or fragments or derivatives thereof, linked to a drug, a toxin, a cytokine, an aptamer, a nucleic acid such as a desoxyribonucleic acid (DNA) or ribonucleic acid (RNA), a therapeutic polypeptide, a radioisotope or a label). Said scaffold protein formats may comprise, for example, ankyrin and affilin proteins and others.

As used herein, the term "Fab" relates to an IgG fragment comprising the antigen binding region, said fragment being composed of one constant and one variable domain from each heavy and light chain of the antibody As used herein, the term "F(ab)$_2$" relates to an IgG fragment consisting of two Fab fragments connected to one another by disulfide bonds.

As used herein, the term "scFv" relates to a single-chain variable fragment being a fusion of the variable regions of the heavy and light chains of immunoglobulins, linked together with a short linker, usually comprising serine (S) and/or glycine (G) residues. This chimeric molecule retains the specificity of the original immunoglobulin, despite removal of the constant regions and the introduction of a linker peptide.

Modified antibody formats are for example bi- or trispecific antibody constructs, antibody-based fusion proteins, immunoconjugates and the like.

IgG, scFv, Fab and/or F(ab)$_2$ are antibody formats which are well known to the skilled person. Related enabling techniques are available from respective textbooks.

Monoclonal antibodies (mAb) derived from mouse may cause unwanted immunological side-effects due to the fact that they contain a protein from another species which may elicit antibodies. In order to overcome this problem, antibody humanization and maturation methods have been designed to generate antibody molecules with minimal immunogenicity when applied to humans, while ideally still retaining specificity and affinity of the non-human parental antibody (for review see Almagro and Fransson 2008). Using these methods, e.g., the framework regions of a mouse mAb are replaced by corresponding human framework regions (so-called CDR grafting). WO200907861 discloses the generation of humanized forms of mouse antibodies by linking the CDR regions of non-human antibodies to human constant regions by recombinant DNA technology. U.S. Pat. No. 6,548,640 by Medical Research Council describes CDR grafting techniques, and U.S. Pat. No. 5,859, 205 by Celltech describes the production of humanised antibodies.

Humanization by CDR grafting, however, often leads to a significant reduction or even loss of binding affinity, as a set of supporting framework residues in the so-called Vernier zone are important for maintaining the conformation of the CDRs (Foote and Winters 1992). These residues are responsible for stabilizing the hypervariable loop structure and modifying their positioning; they fine-tune the antibody affinity. Reintroducing murine residues into the human framework (Queen et al 1989) can address this problem. Such substitutions are commonly called "back-mutations".

Immunogenicity is the ability to induce a T-helper (Th) cell response which is triggered when a unique T cell receptor recognizes a peptide bound to HLA (human leukocyte antigen) class II molecules displayed on antigen presenting cells (APCs). The peptides are generated from proteins internalized by the antigen presenting cells which are then processed through the endosomal cleavage pathway. Only peptides with sufficient affinity for the HLA class II molecules will be presented on the cell surface of APCs and could possibly trigger a Th response.

Using a process known as deimmunization it is possible to further lower the immunogenic potential by removing Th epitopes (Chamberlain 2002; Baker and Jones 2007). This is achieved by predicting which peptides in the respective therapeutic protein can bind to HLA class II molecules, and subsequently introducing substitutions that eliminate or reduce the peptide binding affinity for HLA class II molecules.

There are several HLA class II genes, and HLA class II molecules consist of an alpha and a beta chain, each expressed from a different gene, increasing variation (DRA/DRB, DQA/DQB, and DPA/DPB) and almost all are highly polymorphic; only DRA is non-polymorphic. The focus during deimmunization lies on the DR allotypes which are known to express at higher levels than DQ and DP. The assessment of relevance of individual epitopes is based on the criteria of promiscuity, i.e., the number of HLA allotypes a specific epitope binds to, as well as the importance (frequency) of the allotypes in the population and a qualitative assessment of the HLA-peptide complex binding strength. As the T-cell population of an individual has been selected to not recognize "self-peptides" of endogenous proteins like antibodies, it is possible to screen the protein to be deimmunized for peptides that correspond to (known) self-peptides which should not normally induce a Th response.

As used herein, the term "humanized antibody" relates to an antibody, a fragment or a derivative thereof, in which at least a portion of the constant regions and/or the framework regions, and optionally a portion of CDR regions, of the antibody is derived from or adjusted to human immunoglobulin sequences.

Sequence variants of nucleic acid or amino acid sequences claimed herein that are, e.g., defined by the claimed % sequence identity (homology), and that maintain said properties of the antibodies, fragments or derivatives of the antibodies according to the present invention are also included in the scope of the invention. The term "sequence identity" relates to the percentage of identical nucleotides or amino acids when carrying out a sequence alignment.

As used herein, the term "amino acid substitution" relates to modifications of the amino acid sequence of the protein, wherein one or more amino acids are replaced with the same number of different amino acids, producing a protein which contains a different amino acid sequence than the original protein. A conservative amino acid substitution is understood to relate to a substitution which due to similar size, charge, polarity and/or conformation does not significantly affect the structure and function of the protein. Groups of conservative amino acids in that sense represent, e.g., the non-polar amino acids Gly, Ala, Val, Ile and Leu; the aromatic amino acids Phe, Trp and Tyr; the positively charged amino acids Lys, Arg and His; and the negatively charged amino acids Asp and Glu.

The present invention relates to a humanized antibody, or antibody fragment or antibody derivative thereof, that binds to the extracellular domain of prostate specific membrane antigen (PSMA).

In the following, preferred CDR sequences will be discussed. It is important to understand that the CDRs are comprised in a suitable protein framework so as to be capable to the extracellular domain of prostate specific membrane antigen (PSMA).

The present invention also provides a humanized antibody, or antibody fragment or antibody derivative thereof, that binds to the extracellular domain of PSMA, comprising a VH domain that comprises CDR sequences of $GX_1TX_2TX_3X_4$ (CDR H1), wherein $X_1$, $X_2$, $X_3$ and $X_4$ each are Y, F, W, $GISPGDX_5NX_6NYX_7X_8X_9FX_{10}G$ (CDR H2), wherein $X_5$ is G, S; $X_6$ is T, V; $X_7$ is N, A; $X_8$ is E, Q; $X_9$ is N, K; $X_{10}$ is K, Q; and $DGNX_{11}PX_{12}X_{13}AMDS$ (CDR H3), wherein $X_{11}$, $X_{12}$, $X_{13}$ each are Y, F, W.

The present invention also provides said humanized antibody, or antibody fragment or antibody derivative thereof, wherein the VH domain comprises the CDR H1 sequence GYTFTYF (SEQ ID No. 1).

The present invention further provides said humanized antibody, or antibody fragment or antibody derivative thereof, binding to the extracellular domain of PSMA, wherein the VH domain comprises the CDR H2 sequence SEQ ID No. 2 or SEQ ID No. 7 or SEQ ID No. 9 or SEQ ID No. 11.

The present invention further relates to said humanized antibody, or antibody fragment or antibody derivative thereof, binding to the extracellular domain of PSMA, wherein the VH domain comprises the CDR H3 sequence DGNFPYYAMDS (SEQ ID No. 3).

In a preferred embodiment, the antibody, or antibody fragment or antibody derivative thereof, binding to the extracellular domain of PSMA, comprises a VH domain comprising SEQ ID No. 1 and SEQ ID No. 2 or SEQ ID No. 7 or SEQ ID No. 9 or SEQ ID No. 11 and SEQ ID No. 3.

In a further preferred embodiment, the antibody, or antibody fragment or antibody derivative thereof, binding to the extracellular domain of PSMA, comprises a $V_H$ domain comprising any of the sequences SEQ ID Nos. 13, 15, 17 or 19.

The present invention also relates to a humanized antibody, or antibody fragment or antibody derivative thereof, that binds to the extracellular domain of PSMA, comprising a $V_L$ domain that comprises CDR sequences of $RSSQSLVHSX_1GX_2TX_3LH$ (CDR L1), wherein $X_1$ is N, S; $X_2$ is N, Q; $X_3$ is Y, F, W, $TVSNRX_4S$ (CDR L2), wherein $X_4$ is A, Y, F, W, and

SQSTHVPT (CDR L3).

In a preferred embodiment, said antibody, or antibody fragment or antibody derivative thereof, comprises a VL domain that comprises CDR L1 sequence SEQ ID No. 4 or SEQ ID No. 8 or SEQ ID No. 10.

In a further preferred embodiment, said antibody, or antibody fragment or antibody derivative thereof, comprises a VL domain that comprises CDR L2 sequence SEQ ID No. 5 or SEQ ID No. 12.

In a further preferred embodiment, said antibody, or antibody fragment or antibody derivative thereof, comprises a VL domain that comprises a combination of SEQ ID No. 4 or SEQ ID No. 8 or SEQ ID No. 10, and
SEQ ID No. 5 or SEQ ID No. 12, and
SEQ ID No. 6.

The invention particularly relates to an antibody, or antibody fragment or antibody derivative thereof, comprising a VL domain that comprises any of the sequences SEQ ID Nos. 14, 16, 18 or 20.

The invention also relates to an antibody, or antibody fragment or antibody derivative thereof, comprising a combination of at least one of the VH CDR sequences mentioned above and at least one of the VL CDR sequences mentioned above.

The invention also relates to said antibody, or antibody fragment or antibody derivative thereof, comprising a combination of at least one of the VH domain sequences selected from the group consisting of SEQ ID No. 13, 15, 17 and 19 and at least one of the VL domain sequences selected from the group consisting of SEQ ID No. 14, 16, 18 and 20.

The invention also relates to any such antibody, or antibody fragment or antibody derivative thereof described above, wherein the same binds to the extracellular domain of PSMA with an affinity of $EC_{50}$<0.4 µg/ml, preferably an affinity of $EC_{50}$<0.3 µg/ml, most preferably an affinity of $EC_{50}$<0.4 µg/ml.

Said humanized anti-PSMA antibody, or antibody fragment or antibody derivative thereof, can be glycosylated. The glycan can be an N-linked oligosaccharide chain at asparagin 297 of the heavy chain.

Said prostate specific membrane antigen can be a mammalian, non-primate, primate, and in particular a human prostate specific membrane antigen.

The antibody, or antibody fragment or antibody derivative thereof, according to the present invention can be a monoclonal antibody. The antibody can be of the IgA, IgD, IgE, IgG or IgM isotype.

The present invention relates to an antibody fragment that is selected from the group consisting of a variable domain (Fv), a Fab fragment and an F(ab)$_2$ fragment. The present invention also relates to an antibody derivative that is preferably a single-chain Fv (scFv).

In a preferred embodiment, the humanized antibody, or fragment or derivative thereof, such as a scFv, described in this application specifically bind to native cell-surface PSMA and therefore will have value in diagnostic and therapeutic applications focusing on PSMA as a target antigen for, e.g., prostate cancer. Since PSMA is expressed on prostate cancer cells with a specific tertiary and quaternary structure, particularly antibodies against this cellular conformation can recognize and strongly bind to viable prostate cancer cells and PSMA expressing tissue. Therefore, one aim of the present study was to generate such antibodies, or fragments or derivatives thereof, that can be used for therapeutic and diagnostic targeting of prostate cancer.

In a preferred embodiment, the invention furthermore relates to an antibody-drug conjugate (ADC, also termed immunoconjugate) comprising the humanized antibody, or a fragment or derivative thereof, as described above, conjugated to a therapeutic agent, optionally via a linker moiety.

Said therapeutic agent could be, e.g., a drug, a chemotherapeutic agent, a cytotoxic agent such as for example taxol, cytocalasin B, gramicidin D, a toxin, a growth inhibitory agent, an aptamer, a nucleic acid such as a desoxyribonucleic acid (DNA) or ribonucleic acid (RNA), a therapeutic polypeptide, or a radioactive substance.

The ADC can comprise a linker region between the therapeutic agent and the anti-PSMA antibody, or antibody fragment or antibody derivative thereof. The linker can be cleavable by, for example but not limited to, a cleaving agent or acidic pH conditions.

In another aspect of the present invention, a humanized anti-PSMA antibody, or fragment or derivative thereof, is provided, said antibody being formulated in a pharmaceutical formulation.

In aqueous form, said pharmaceutical formulation may be ready for administration, while in lyophilised form said formulation can be transferred into liquid form prior to administration, e.g., by addition of water for injection which may or may not comprise a preservative such as for example, but not limited to, benzyl alcohol, antioxidants like vitamin A, vitamin E, vitamin C, retinyl palmitate, and selenium, the amino acids cysteine and methionine, citric acid and sodium citrate, synthetic preservatives like the parabens methyl paraben and propyl paraben.

Said pharmaceutical formulation may further comprise one or more stabilizer, which may be, e.g., an amino acid, a sugar polyol, a disaccharide and/or a polysaccharide. Said pharmaceutical formulation may further comprise one or more surfactant, one or more isotonizing agents, and/or one or more metal ion chelator, and/or one or more preservative.

The pharmaceutical formulation as described herein can be suitable for at least intravenous, intramuscular or subcutaneous administration. Alternatively, the antibody according to the present invention may be provided in a depot formulation which allows the sustained release of the biologically active agent over a certain period of time.

In still another aspect of the present invention, a primary packaging, such as a prefilled syringe or pen, a vial, or an infusion bag is provided, which comprises said formulation according to the previous aspect of the invention and/or said humanized anti-PSMA antibody, or fragment or derivative thereof.

The prefilled syringe or pen may contain the formulation either in lyophilised form (which has then to be solubilised, e.g., with water for injection, prior to administration), or in aqueous form. Said syringe or pen is often a disposable article for single use only, and may have a volume between 0.1 and 20 ml. However, the syringe or pen may also be a multi-use or multi-dose syringe or pen.

Said vial may also contain the formulation in lyophilised form or in aqueous form and may serve as a single or multiple use device. As a multiple use device, said vial can have a bigger volume. Said infusion bag usually contains the formulation in aqueous form and may have a volume between 20 and 5000 ml.

Said pharmaceutical formulation is intended for the treatment of a medical disorder associated with overexpression of PSMA and comprises a humanized antibody, or fragment or antibody derivative thereof, as described herein, together with at least a pharmaceutically acceptable carrier.

Said medical disorder associated with overexpression of PSMA can be, e.g., prostate cancer or a neurologic disorder. Humanized anti-PSMA antibodies, or fragments or derivatives thereof, can mediate antitumoral effects by activating humoral or cellular immune functions, or by targeting tumors with conjugated cytotoxins or radioactivity as described above.

The present invention relates to an antibody, or antibody fragment or antibody derivative thereof, as described herein for use in the treatment of prostate cancer.

The present invention also relates to a method of treating a patient suffering from prostate cancer comprising administering an effective amount of an antibody, or antibody fragment or antibody derivative thereof, as described herein.

Another aspect of the present invention relates to a diagnostic kit for the detection of tumor cells comprising an isolated monoclonal antibody, or an antigen binding fragment or derivative thereof, allowing for the detection of the same after binding with suitable detection reagents and devices. The invention provides also a method for the in vitro identification of tumor cells by which the tumor cells to be identified are contacted with an isolated monoclonal antibody, or an antigen binding fragment or derivative thereof, which carries a label which can be detected by suitable analytical devices. The label allows the diagnostic identification of tumor cells, for example in sections of human tissues obtained after surgery or biopsy.

The present invention also relates to a host cell capable of producing said humanized anti-PSMA antibodies, or fragments or derivatives thereof, and to a cell line transfected with a recombinant plasmid containing coding sequences of said antibodies of the present invention.

According to another preferred embodiment of the present invention, said host cell is a mammalian cell. According to still another preferred embodiment of the present invention, said host cell is at least one selected from the group comprising, e.g., Baby Hamster Kidney cells (e.g., BHK21), Chinese Hamster Ovary cells (CHO), mouse myeloma cells (e.g., SP2/0 or NS0), human embryonic kidney cells (e.g., HEK-293), human retina-derived cells (e.g., PER-C6), and amniocyte cells (e.g., CAP).

In one embodiment, the mammalian cell is a CHO cell line (e.g., CHO-K1, CHO-DG44, CHO-DXB, or CHO-dhfr⁻).

The present invention also relates to a nucleic acid encoding for a humanized antibody, an antibody fragment or antibody derivative thereof, binding to PSMA as described in the present application.

In one embodiment, the present invention relates to a humanized antibody, or antibody fragment or antibody derivative thereof, comprising a variable heavy (VH) domain comprising
  a CDR H1 sequence according to SEQ ID No. 1,
  a CDR H2 sequence selected from any of the sequences according to SEQ ID No. 2, SEQ ID No. 7, SEQ ID No. 9, and SEQ ID No. 11,
  a CDR H3 sequence according to SEQ ID No. 3, and a variable light (VL) domain comprising
  a CDR L1 sequence selected from any of the sequences according to SEQ ID No. 4, SEQ ID No. 8, and SEQ ID No. 10,
  a CDR L2 sequence selected from any of the sequences according to SEQ ID No. 5 and SEQ ID No. 12, and
  a CDR L3 sequence according to SEQ ID No. 6,
  but not comprising the combination of a CDR H1 sequence according to SEQ ID No. 1, a CDR H2 sequence according to SEQ ID No. 2, a CDR H3 sequence according to SEQ ID No. 3, a CDR L1 sequence according to SEQ ID No. 4, a CDR L2 sequence according to SEQ ID No. 5, and a CDR L3 sequence according to SEQ ID 6,
  that binds to the extracellular domain of prostate specific membrane antigen (PSMA).

For the avoidance of doubt, all possible 24 combinations of said CDRs (i.e., combinations of one CDR H1, one CDR H2, one CDR H3, one CDR L1, one CDR L2, and one CDR L3) are deemed to be individually disclosed herewith in the present specification.

In one embodiment, the present invention relates to a humanized antibody, or antibody fragment or antibody derivative thereof, comprising a VH domain having at least 90%, preferably 95%, sequence homology to a sequence selected from any of the sequences according to SEQ ID No. 13, SEQ ID No. 15, SEQ ID No. 17, and SEQ ID No. 19.

In one embodiment, the present invention relates to a humanized antibody, or antibody fragment or antibody derivative thereof, comprising a VH domain sequence selected from any of the sequences according to SEQ ID No. 13, SEQ ID No. 15, SEQ ID No. 17, and SEQ ID No. 19.

In one embodiment, the present invention relates to a humanized antibody, or antibody fragment or antibody derivative thereof, comprising a VL domain having at least 90%, preferably 95%, sequence homology to a sequence selected from any of the sequences according to SEQ ID No. 14, SEQ ID No. 16, SEQ ID No. 18, and SEQ ID No. 20.

In one embodiment, the present invention relates to a humanized antibody, or antibody fragment or antibody derivative thereof, comprising a VL domain sequence selected from any of the sequences according to SEQ ID No. 14, SEQ ID No. 16, SEQ ID No. 18, and SEQ ID No. 20.

In one embodiment, the present invention relates to a humanized antibody, or antibody fragment or antibody derivative thereof, comprising the VH domain sequence according to SEQ ID No. 13 and a VL domain sequence selected from any of the sequences according to SEQ ID No. 14, SEQ ID No. 16, SEQ ID No. 18, and SEQ ID No. 20, or the VH domain sequence according to SEQ ID No. 15 and a VL domain sequence selected from any of the sequences according to SEQ ID No. 14, SEQ ID No. 16, SEQ ID No. 18, and SEQ ID No. 20, or the VH domain sequence according to SEQ ID No. 17 and a VL domain sequence selected from any of the sequences according to SEQ ID No. 14, SEQ ID No. 16, SEQ ID No. 18, and SEQ ID No. 20, or the VH domain sequence according to SEQ ID No. 19 and a VL domain sequence selected from any of the sequences according to SEQ ID No. 14, SEQ ID No. 16, SEQ ID No. 18, and SEQ ID No. 20.

In one embodiment, the present invention relates to a humanized antibody, or antibody fragment or antibody derivative thereof, wherein the heavy chain comprises any of the sequences SEQ ID No. 21, SEQ ID No. 23, SEQ ID No. 25, or SEQ ID No. 27.

In one embodiment, the present invention relates to a humanized antibody, or antibody fragment or antibody derivative thereof, wherein the light chain comprises any of the sequences SEQ ID Nos. 22, SEQ ID No. 24, SEQ ID No. 26, or SEQ ID No. 28.

In one embodiment, the present invention relates to a humanized antibody, or antibody fragment or antibody derivative thereof, comprising at least one heavy chain comprising any of the sequences SEQ ID Nos. 21, 23, 25 or 27, and at least one light chain comprising any of the sequences SEQ ID Nos. 22, 24, 26 or 28.

In a preferred embodiment, the present invention relates to a humanized antibody, or antibody fragment or antibody derivative thereof, comprising at least one heavy chain comprising SEQ ID No. 27 and at least one light chain comprising SEQ ID No. 28.

In one embodiment, the present invention relates to a humanized antibody, or antibody fragment or antibody derivative thereof, according to the present invention, binding to the extracellular domain of PSMA with an affinity of $EC_{50}$<0.4 µg/ml.

In one embodiment, the present invention relates to a humanized antibody, or antibody fragment or antibody derivative thereof, according to the present invention, wherein the antibody is glycosylated. Said glycosylation can relate to a glycan which is an N-linked oligosaccharide chain at asparagin 297 of the heavy chain.

In one embodiment, the present invention relates to a humanized antibody, or antibody fragment or antibody derivative thereof, according to the present invention, wherein said prostate specific membrane antigen is human prostate specific membrane antigen.

The humanized antibody, or antibody fragment or antibody derivative thereof, according to the present invention can be a monoclonal antibody, or antibody fragment or antibody derivative thereof. Said monoclonal antibody can preferably be of the isotype IgG.

The humanized antibody fragment according to the present invention can be selected from the group consisting of a variable domain (Fv), a Fab fragment and an $F(ab)_2$ fragment.

The humanized antibody derivative according to the present invention can be a single-chain Fv (scFv).

In one embodiment, the present invention relates to an antibody-drug conjugate (ADC) comprising the humanized antibody, or a fragment or derivative thereof, according to the present invention conjugated to a therapeutic agent, optionally via a linker moiety.

In one embodiment, the present invention relates to a pharmaceutical formulation for the treatment of a medical disorder associated with overexpression of PSMA comprising a humanized antibody, or antibody fragment or antibody derivative thereof, according to the present invention, together with at least a pharmaceutically acceptable carrier. Said medical disorder associated with overexpression of PSMA can be prostate cancer. Said pharmaceutical formulation according to the present invention can be a formulation that is suitable for at least intravenous, intramuscular or subcutaneous administration.

In one embodiment, the present invention relates to a humanized antibody, or antibody fragment or antibody derivative thereof, according to the present invention for use in the treatment of prostate cancer.

In one embodiment, the present invention relates to a method of treating a patient suffering from prostate cancer comprising administering an effective amount of a humanized antibody, or antibody fragment or antibody derivative thereof, according to the present invention to the patient.

In one embodiment, the present invention relates to a nucleic acid encoding for a humanized antibody, an antibody fragment or antibody derivative thereof, according to the present invention.

In one embodiment, the present invention relates to a host cell capable of producing a humanized antibody, an antibody fragment or antibody derivative thereof, according to the present invention. Said host cell according to the present invention can be a mammalian cell. Said mammalian cell according to the present invention preferably is a CHO cell line.

The antibodies or fragments or derivatives of the present invention may be produced by transfection of a host cell with an expression vector comprising the coding sequence for the antibody according to the invention. The expression vector or recombinant plasmid is produced by placing the coding antibody sequences under control of suitable regulatory genetic elements, including promoter and enhancer sequences like, e.g., a CMV promoter. Heavy and light chain sequences might be expressed from individual expression vectors which are co-transfected, or from dual expression vectors. Said transfection may be a transient transfection or a stabile transfection. The transfected cells are subsequently cultivated to produce the transfected antibody construct. When stabile transfection is performed, then stable clones secreting antibodies with properly associated heavy and light chains are selected by screening with an appropriate assay, such as, e.g., ELISA, subcloned, and propagated for future production.

EXAMPLES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

All amino acid sequences disclosed herein are shown from N-terminus to C-terminus; all nucleic acid sequences disclosed herein are shown 5'→3'.

Example 1: Humanization and Deimmunization of Murine Antibody 3F11

The murine anti-PSMA antibody 3/F11 (Wolf et al., 2010a; EP 1883698 B2) was subjected to humanization by grafting of the complementarity determining regions (CDRs) into a selected acceptor framework from the set of human germlines.

Epibase™ immunoprofiling of parental 3/F11 against 85 HLA class II allotypes was performed, analyzing epitopes or clusters of adjoining epitopes for possible substitutions that would remove or reduce binding to HLA allotypes with a focus on HLA-DRB1 allotypes. Critical positions making up the VH/VL inter-chain interface or are responsible for the discrete set of canonical structures of CDRs were identified. Based on sequence alignment of the parental antibody sequence to human germline sequences, the closest matching, optimal human germline sequence as acceptor was identified, taking particularly sequence identity across the framework, identical or compatible inter-chain interface residues, support loops with the parental CDR canonical conformations and the combination of heavy and light germlines found in expressed antibodies into consideration. 3/F11 was found to be most compatible to the human light chain germline VK2-A17 and heavy chain germline VH1-1-69 of the VK2 light chain germline family VK2 and the human heavy chain germline family VH1, respectively. For CDR grafting, amino acids in the parental framework that differ from the chosen acceptor were replaced with the corresponding human amino acid.

Sequences were analyzed for potential post-translational modification sites (asparagine deamidation, aspartate isomerization, C-terminal lysine clipping, free Cys thiol groups, N- and O-glycosylation, N-terminal cyclization, oxidation and pyroglutamate formation) that might cause problems during development of a therapeutic product. Structural models of the Fv-region of 3/F11 and variants were generated using an in-silico modelling platform, and candidate structural fragments for the frameworks and CDRs as well as the full Fv were scored and ranked.

Figure 4:
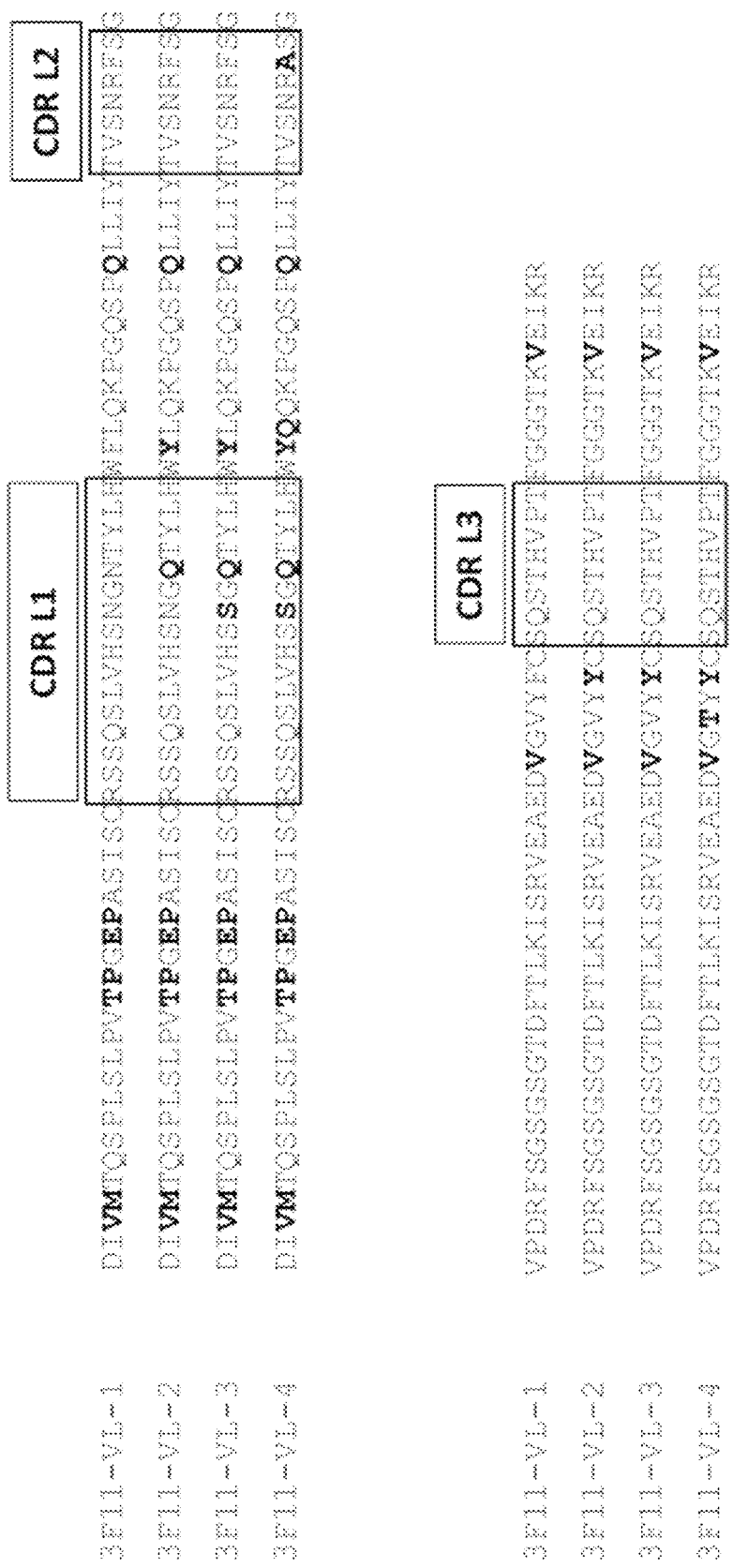
FIG. 4. Sequence alignment of variable light chain ($V_L$) regions of humanized/deimmunized variants of antibody 3F11. Amino acid substitutions versus murine 3F11-wt are in bold.

In order to evaluate the impact of all substitutions considered in an effective manner, substitutions were grouped where appropriate, and a total of four humanized/deimmunized light chains and four humanized/deimmunized heavy chains were selected. Table 2 lists the name of the engineered amino acid chains along with a description of the modifications. The amino acid sequences of the engineered chains are given in Table 1. Sequence alignments of the humanized/deimmunized light and heavy chains, respectively, are shown in FIGS. 3 and 4.

Heavy chain variable domain variant 3F11-VH-1 comprises all three CDRs of the parental murine VH sequence. In variant 3F11-VH-2, two CDRs are identical to the parental murine VH sequence, whereas the CDR H2 differs in four positions from the parental murine sequence (aa 61-63: NEN>AQK, aa 65: K>Q). In variant 3F11-VH-3, again two CDRs are identical to the parental murine VH sequence, whereas the CDR H2 differs in five positions from the parental murine sequence (aa 58: T>V, aa 61-63: NEN>AQK, aa 65: K>Q). In variant 3F11-VH-4, again two CDRs are identical to the parental murine VH sequence, whereas the CDR H2 differs in six positions from the parental murine sequence (aa 56: G>S, aa 58: T>V, aa 61-63: NEN>AQK, aa 65: K>Q).

Light chain variable domain variant 3F11-VL-1 comprises all three CDRs of the parental murine VL sequence. In variant 3F11-VL-2, two CDRs are identical to the parental murine VL sequence, whereas the CDR L1 comprises a substitution at amino acid No. 35 (N>Q). In variant 3F11-VL-3, two CDRs are identical to the parental murine VL sequence, whereas the CDR L1 differs in two positions from the parental murine sequence (aa 33: N>S, aa 35: N>Q). In variant 3F11-VL-4, CDR L1 differs in two positions (aa 33: N>S, aa 35: N>Q) and CDR L2 differs in one position (aa 60: F>A) from the parental murine sequence, and CDR L3 is identical to the parental murine sequence.

TABLE 2

CDR composition of 3F11 wt and humanized/deimmunized 3F11 variants with respective substitutions (amino acid numbering according to Kabat et al.)

| Chain | CDR H1 | CDR H2 | CDR H3 |
|---|---|---|---|
| 3F11 wt VH | murine | murine | murine |
| 3F11-VH-1 | identical | identical | identical |
| 3F11-VH-2 | identical | aa 61-63: NEN > AQK<br>aa 65: K > Q | identical |
| 3F11-VH-3 | identical | aa 58: T > V<br>aa 61-63: NEN > AQK<br>aa 65: K > Q | identical |
| 3F11-VH-4 | identical | aa 56: G > S<br>aa 58: T > V<br>aa 61-63: NEN > AQK<br>aa 65: K > Q | identical |

| Chain | CDR L1 | CDR L2 | CDR L3 |
|---|---|---|---|
| 3F11 wt VL | murine | murine | murine |
| 3F11-VL-1 | identical | identical | identical |
| 3F11-VL-2 | aa 35: N > Q<br>(optionally aa 41: F > Y) | identical | identical |
| 3F11-VL-3 | aa 33: N > S<br>aa 35: N > Q<br>(optionally aa 41: F > Y) | identical | identical |
| 3F11-VL-4 | aa 33: N > S<br>aa 35: N > Q<br>(optionally aa 41: F > Y)<br>(optionally aa 42: L > Q) | aa 60: F > A | (optionally aa 90: V > T) |

3F11-VL-2 has optionally the following mutation: aa 41: F>Y. 3F11-VL-3 has optionally the following mutation: aa 41: F>Y. 3F11-VL-4 has optionally the following mutations: aa 41: F>Y; aa 42: L>Q; and/or aa 90: V>T.

For evaluating the impact of substitution combinations, an experimental design of variant combination was set up as outlined in Table 3. By combination of the four humanized/deimmunized heavy chains and four humanized/deimmunized light chains, 16 different humanized/deimmunized full-length antibodies were derived, which are termed as shown in Table 3.

TABLE 3

Combinations of 3F11 humanized/deimmunized variant VH and VL chains forming 16 different variants of humanized variant domains and full-length antibodies, respectively. 3F11 wt is comprising murine VH and VL chains.

| Variant Name | Light Chain Name | Heavy Chain Name |
|---|---|---|
| 3F11 wt | 3F11-VL | 3F11-VH |
| 3F11-var 1 | 3F11-VL-1 | 3F11-VH-1 |
| 3F11-var 2 | 3F11-VL-1 | 3F11-VH-2 |
| 3F11-var 3 | 3F11-VL-1 | 3F11-VH-3 |
| 3F11-var 4 | 3F11-VL-1 | 3F11-VH-4 |
| 3F11-var 5 | 3F11-VL-2 | 3F11-VH-1 |
| 3F11-var 6 | 3F11-VL-2 | 3F11-VH-2 |
| 3F11-var 7 | 3F11-VL-2 | 3F11-VH-3 |
| 3F11-var 8 | 3F11-VL-2 | 3F11-VH-4 |
| 3F11-var 9 | 3F11-VL-3 | 3F11-VH-1 |
| 3F11-var 10 | 3F11-VL-3 | 3F11-VH-2 |
| 3F11-var 11 | 3F11-VL-3 | 3F11-VH-3 |
| 3F11-var 12 | 3F11-VL-3 | 3F11-VH-4 |
| 3F11-var 13 | 3F11-VL-4 | 3F11-VH-1 |
| 3F11-var 14 | 3F11-VL-4 | 3F11-VH-2 |
| 3F11-var 15 | 3F11-VL-4 | 3F11-VH-3 |
| 3F11-var 16 | 3F11-VL-4 | 3F11-VH-4 |

The predicted critical epitopes of HLA DRB1, DRB3/4/5, DQ and DP for the parental and humanized/deimmunized sequences are presented in Table 4. The differences between the parental and variant antibodies in Table 4 account for the respective removal of potential epitopes.

TABLE 4

Predicted critical epitope counts of HLA DRB1, DRB3/4/5, DQ and DP for the parental and humanized/deimmunized sequences

| Variant Name | DRB1 | DRB3/4/5 | DQ | DP |
|---|---|---|---|---|
| 3-F11 | 57 (7) | 30 (2) | 1 (0) | 2 (0) |
| 3-F11_var1 | 41 (22) | 25 (12) | 1 (0) | 2 (0) |
| 3-F11_var2 | 38 (25) | 21 (15) | 1 (1) | 2 (0) |
| 3-F11_var3 | 40 (24) | 24 (14) | 1 (1) | 2 (0) |
| 3-F11_var4 | 40 (24) | 24 (14) | 1 (1) | 2 (0) |
| 3-F11_var5 | 40 (24) | 22 (13) | 0 (1) | 2 (0) |
| 3-F11_var6 | 37 (27) | 18 (16) | 0 (2) | 2 (0) |
| 3-F11_var7 | 39 (26) | 21 (15) | 0 (2) | 2 (0) |
| 3-F11_var8 | 39 (26) | 21 (15) | 0 (2) | 2 (0) |

TABLE 4-continued

Predicted critical epitope counts of HLA DRB1, DRB3/4/5, DQ and DP for the parental and humanized/deimmunized sequences

| Variant Name | DRB1 | DRB3/4/5 | DQ | DP |
|---|---|---|---|---|
| 3-F11_var9 | 41 (24) | 23 (13) | 0 (1) | 2 (0) |
| 3-F11_var10 | 38 (27) | 19 (16) | 0 (2) | 2 (0) |
| 3-F11_var11 | 40 (26) | 22 (15) | 0 (2) | 2 (0) |
| 3-F11_var12 | 40 (26) | 22 (15) | 0 (2) | 2 (0) |
| 3-F11_var13 | 40 (22) | 21 (12) | 1 (0) | 2 (0) |
| 3-F11_var14 | 37 (25) | 17 (15) | 1 (1) | 2 (0) |
| 3-F11_var15 | 39 (24) | 20 (14) | 1 (1) | 2 (0) |
| 3-F11_var16 | 39 (24) | 20 (14) | 1 (1) | 2 (0) |

Critical epitope counts per gene family, peptides binding to multiple allotypes of the same group were counted as one. Numbers between brakcets refer to additional self-epitopes.

Example 2: Expression and Purification of Humanized Anti-PSMA Antibody Variants The heavy and light chain variable domains for the antibodies were synthesized and subcloned into GS Xceed™ vectors (Lonza). Light chain variable domain encoding regions were transferred into pXC-Kappa and heavy chain variable domain encoding regions into pXC-IgG1zadeltaK vectors, respectively.

Single gene vectors (SGVs) were transiently co-transfected into Chinese Hamster Ovary GS knock-out cells (CHOK1SV GS-KO) alongside the reference murine antibody at 200-ml scale. Transient transfections were performed via electroporation (Gene Pulse XCell, BioRad) using CHOK1SV GS-KO cells which had been in culture for a minimum of two weeks. Cells were subcultured 24 hours prior to transfection and cell viability was >99% at the time of transfection. Six days post-transfection, cell viability and viable cell concentrations were measured at the time of harvest. Cells were found to be in the range of 4.4-7.5×10$^6$ viable cells/ml with viabilities ranging from 89.0-96.1%.

The clarified supernatants were purified by protein A chromatography using pre-packed 5-ml HiTrap Mab Select SuRE columns on an AKTA purifier by standard procedures. Upon elution with 10 mM sodium formate, pH 3.5, the pH of the protein containing fractions was adjusted immediately by addition of 2× phosphate-buffered saline (PBS) to yield final buffer conditions of 1×PBS, 5 mM sodium formate, pH 7.4. Table 5 below shows titers and product yields for the 3F11 parental murine antibody and the various humanized antibody variants.

As a surprising effect, the inventors observed significantly higher expression titers for some of the humanized anti-PSMA antibody variants as compared to the parental murine 3F11 antibody (see Table AA). With humanized variants 3F11_var2, 3F11_var6, 3F11_var9, 3F11_earl 1, 3F11_var13, 3F11_var15 and 3F11_var16, expression titers of 9.5-13 mg/liter were obtained, as compared to 3.88 mg/liter for the parental murine 3F11 antibody. Due to the increase of expression titers by a factor of 3-4, production costs for humanized/deimmunized variant-based therapeutic products can be expected to be considerably reduced.

TABLE 5

Results of characterization of humanized 3F11 antibody variants

| Sample | Heavy chain | Light chain | Titre[#] (mg/L) | Yield[#] (mg) | Percentage Monomer[#] (%) | $EC_{50}$ (µg/ml) |
|---|---|---|---|---|---|---|
| 3F11_wt | VH | VL | 3.88 | 0.78 | 98.09 | 0.4189 |
| 3F11_var1 | VH1 | VL1 | 2.65 | 0.53 | 99.50 | 0.2897 |
| 3F11_var2 | VH2 | VL1 | 11.00 | 2.20 | 97.20 | 0.2730 |
| 3F11_var3 | VH3 | VL1 | 2.90 | 0.58 | 96.78 | 0.2638 |
| 3F11_var4 | VH4 | VL1 | 4.25 | 0.85 | 98.34 | 0.3732 |
| 3F11_var5 | VH1 | VL2 | 3.20 | 0.64 | 98.30 | 0.3038 |
| 3F11_var6 | VH2 | VL2 | 13.05 | 2.61 | 96.73 | 0.2187 |
| 3F11_var7 | VH3 | VL2 | 5.60 | 1.12 | 95.52 | 0.1784 |
| 3F11_var8 | VH4 | VL2 | 1.87 | 0.37 | 94.42 | 0.2040 |
| 3F11_var9 | VH1 | VL3 | 10.65 | 2.13 | 97.90 | 0.2815 |
| 3F11_var10 | VH2 | VL3 | 3.00 | 0.60 | 95.04 | 0.2844 |
| 3F11_var11 | VH3 | VL3 | 12.45 | 2.49 | 96.34 | 0.3394 |
| 3F11_var12 | VH4 | VL3 | 2.64 | 0.53 | 97.75 | 0.3288 |
| 3F11_var13 | VH1 | VL4 | 12.15 | 2.43 | 98.16 | 0.2503 |
| 3F11_var14 | VH2 | VL4 | 3.00 | 0.60 | 96.61 | 0.2715 |
| 3F11_var15 | VH3 | VL4 | 13.00 | 2.60 | 96.81 | 0.2443 |
| 3F11_var16 | VH4 | VL4 | 9.52 | 1.90 | 98.00 | 0.2483 |

[#]as determined post Protein A purification

Example 3: Biochemical Characterization of Humanized Anti-PSMA Antibody Variants Purified samples were analyzed by sodium dodecyl sulphate polyacrylamide gel electrophoresis (SDS-PAGE) and size exclusion (SE)-HPLC on an Agilent 1200 series system using Zorbax GF-250 (9.4 mm ID×25 cm) column (Agilent).

Figure 5:
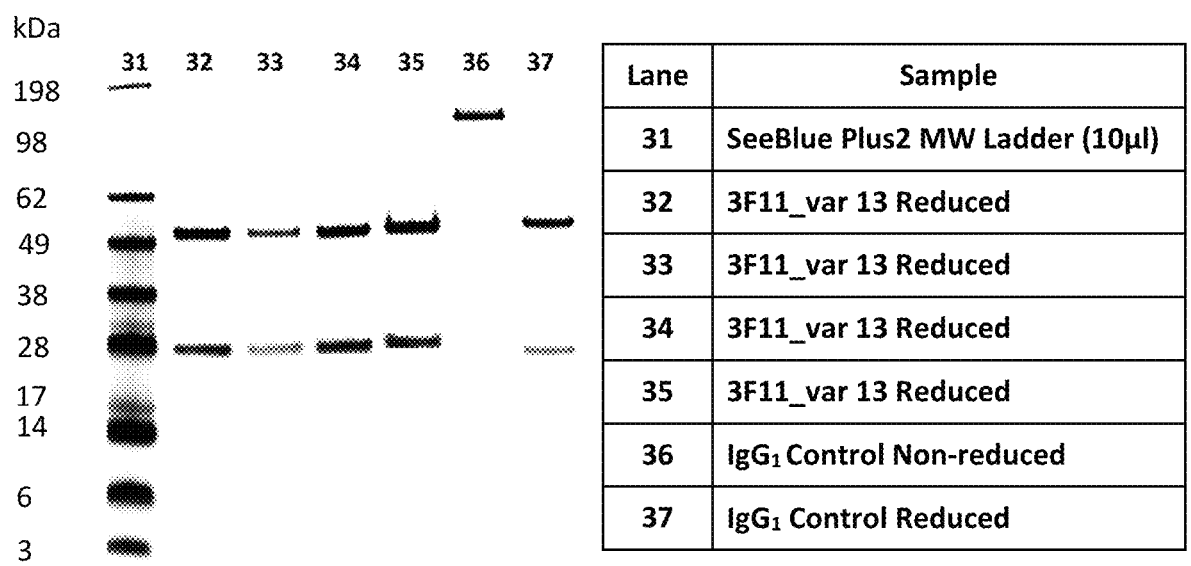
FIG. 5. SDS-PAGE and Coomassie staining for the analysis of humanized 3F11 antibody variants 13-16 under reducing conditions. 1 μg of sample and control was loaded per well on the gel.

In SDS-PAA gels, under non-reducing conditions a signal at >98 kDa was seen for all variants comparable to the control antibody (IgG$_1$) and the parental 3F11, which is consistent with a full-length antibody. Under reducing conditions, a signal at ca. 28 kDa and one signal at ca. 49 kDa can be seen for all variants comparable to the control antibody and the parental 3F11, which is consistent with the sizes of an antibody light and heavy chain, respectively. Representative results are shown in FIG. 5.

Retention times of the humanized 3F11 variant monomeric antibodies (7.96-8.00 min.) in SE-HPLC were comparable to the 3F11 murine parental antibody (7.968 min.). The SE-HPLC chromatographs for all samples showed an additional minor peak at lower retention times (ca. 7.2 min.) with an area of up to 5.4% that corresponds to higher molecular weight impurities such as soluble aggregates.

Example 4: Cell Binding Studies with Humanized Anti-PSMA Antibody Variants

Figure 6:
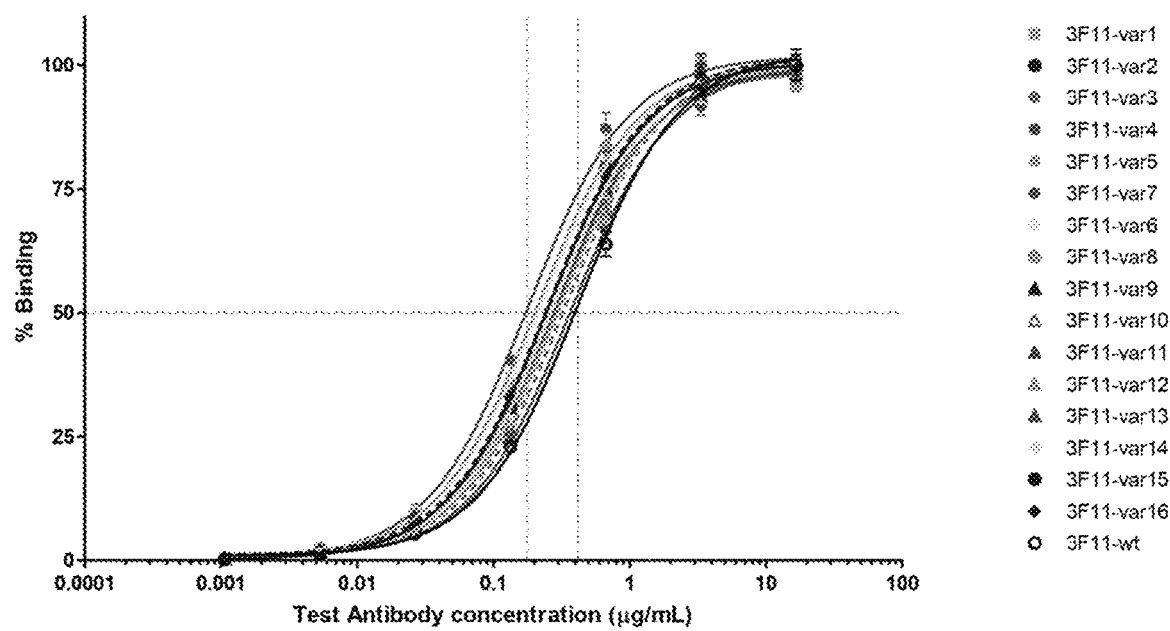
FIG. 6. Binding dose-response curves for humanized 3F11 antibody variants. The symbols represent the mean±SEM of replicate samples (n=2 for humanized samples and n=8 for the chimeric 3F11-wt antibody) for normalized binding data for one experiment. MFI vs. log-dose transformed data was normalized using maximal and minimal MFI values. $R^2 \geq 0.99$ in all cases.

Quality and binding activity of all humanized 3F11 antibody variants were assessed in cell binding assays using the human prostate carcinoma cell line LNCAP (German Collection of Microorganisms and Cell Cultures, DSMZ no. ACC 256) in a 96-well plate-based assay format and cell-based FACS analysis. Pre-confluent LNCAP cells at 80-90% confluence were washed and detached from the plates with trypsin prior to 1-hour incubation at 37° C., 5% $CO_2$ in the flasks to restore cell surface proteins. Cells were washed and adjusted to 1×10$^6$ cells/ml in staining media (RPMI-1640, 25 mM HEPES, 3% h.i. FBS and 0.02% sodium azide). Various concentrations of the monoclonal antibody samples (murine wt and 16 humanized variants) ranging from 50 to 0.0032 µg/ml were prepared in staining media and incubated with the cells in pre-cooled 96-well plates for 30 min. on ice to allow antibody binding to the LNCAP cell surface. Subsequently, cells were washed at 4° C. with PBS to remove free antibody, and bound antibody was labelled with FITC goat anti-human IgG H&L preabsorbed (Abcam) secondary antibody for 30 min. on ice. Finally, cells were washed, fixed and FITC fluorescence associated to the antibody bound to the cells was measured by flow cytometry (GUAVA 8HT Cytometer). Data was analyzed using Incyte GuavaSoft 2.7 software (Merck-Millipore). The obtained dose-response data (plotted as log-transformed dose vs. response) typically produced sigmoidal curves with variable slope which were fitted to a 4-parameter logistic dose-response equation using GraphPad Prism software. The $EC_{50}$ dose, defined as the concentration of antibody that provides half of maximal target cell binding, was used to compare the bioactivity of different antibody variants. Data points represent the average of duplicate wells and standard error of the mean (SEM). Binding curves for the parental 3F11 wt antibody and the sixteen humanized variants are shown in FIG. 6.

Figure 7:
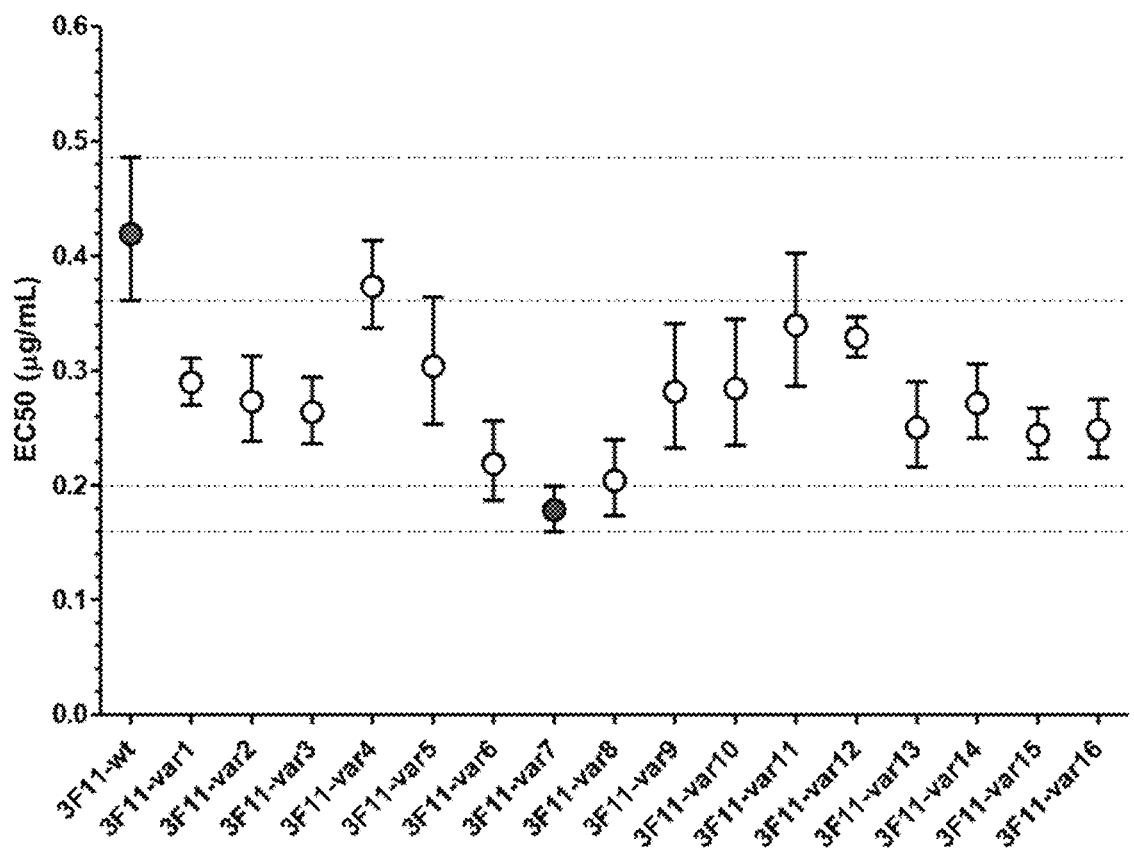
FIG. 7. $EC_{50}$ binding for humanized 3F11 antibody variants. The symbols represent the mean $EC_{50}$ and the bars show the 95% confidence interval (CI). The black dotted lines show the 95% CI for the 3F11-wt antibody (n=8) and the red dotted lines show the 95% CI for the 3F11-var7 (n=1) for one experiment. The variant with the highest binding activity (3F11-var7) and the wt antibody are highlighted with a filled-in symbol.

Quite surprisingly, the cell-based binding assay revealed that all of the sixteen 3F11 humanized variants bind to PSMA-expressing cells with a higher affinity than obtained with the parental murine antibody 3F11. The binding activity ($EC_{50}$) of the humanized variants ranged from 0.1784 to 0.3732 µg/ml and in most cases was significantly higher (based on 95% confidence interval, CI) than that of the parental antibody 3F11 ($EC_{50}$=0.4189 µg/ml). 3F11-var7 showed the highest binding activity ($EC_{50}$=0.1784 µg/ml) closely followed by 3F11-var8 and 3F11-var6 ($EC_{50}$=0.2040 µg/ml and $EC_{50}$=0.2187 µg/ml, respectively, see Table 6). Results from a single experiment are shown in FIG. 7.

TABLE 6

$EC_{50}$ binding activity and 95% CI for humanized 3F11 antibody variants

| Sample | EC50 (µg/ml) | Upper 95% CI (µg/ml) | Lower 95% CI (µg/ml) |
|---|---|---|---|
| 3F11-wt | 0.4189 | 0.4859 | 0.3612 |
| 3F11-var1 | 0.2897 | 0.3109 | 0.2700 |
| 3F11-var2 | 0.2730 | 0.3127 | 0.2384 |
| 3F11-var3 | 0.2638 | 0.2944 | 0.2363 |
| 3F11-var4 | 0.3732 | 0.4134 | 0.3370 |
| 3F11-var5 | 0.3038 | 0.3641 | 0.2534 |
| 3F11-var6 | 0.2187 | 0.2561 | 0.1868 |
| 3F11-var7 | 0.1784 | 0.1992 | 0.1597 |
| 3F11-var8 | 0.2040 | 0.2397 | 0.1736 |
| 3F11-var9 | 0.2815 | 0.3408 | 0.2325 |
| 3F11-var10 | 0.2844 | 0.3445 | 0.2348 |
| 3F11-var11 | 0.3394 | 0.4023 | 0.2883 |
| 3F11-var12 | 0.3288 | 0.3467 | 0.3119 |
| 3F11-var13 | 0.2503 | 0.2902 | 0.2159 |
| 3F11-var14 | 0.2715 | 0.3057 | 0.2412 |
| 3F11-var15 | 0.2443 | 0.2672 | 0.2234 |
| 3F11-var16 | 0.2483 | 0.2751 | 0.2242 |

These findings were particularly unexpected as most of the humanized variants (all variants which did not comprise heavy chain variant 3F11_VH_1) did not require any back-mutations in the framework regions spanning between the CDRs, and especially as none of the variants had been gone through affinity maturations, which is known to be usually required after humanization of antibodies because of significant decrease or loss of affinity. Surprisingly, such additional effort was found not to be required with the procedure for generation of humanized variants and with the variants according to the present invention.

Example 5: Cell Binding Studies with Anti-PSMA scFv Constructs

Combinations of the 3F11-VH-1 and 3F11-VL-1 chains (3F11-var1) and of 3F11-VH-4 and 3F11-VL-4 chains (3F11-var16) were also used for generation of single-chain Fv (scFv) constructs. For both constructs, respective variable domain sequences were cloned in VL-VH composition into the expression vector pHOG21 and expressed in bacterial cells. After affinity chromatographic purification, binding of both scFv constructs to PSMA-expressing cells of the LNCAP sub-cell line C4-2 and to PSMA-negative DU145 prostate cancer cells was tested. Both scFv constructs showed strong binding to C4-2 cells, but no binding to the negative control DU145 cells.

REFERENCES

Almagro J C, Fransson J (2008). Humanization of antibodies. Frontiers in Bioscience Vol. 13:1619-1633.

Baker M P, Jones T D (2007). Identification and removal of immunogenicity in therapeutic proteins. Curr. Opin. Drug Discov. Devel. Vol. 10: 219-227.

Bander N H, Nanus D M, Milowsky M, Kostakoglu L, Vallabahajosula S, Goldsmith S J (2003). Targeted systemic therapy of prostate cancer with a monoclonal antibody to prostate-specific membrane antigen. Seminars in Oncology Vol. 30, No. 5: 667-676.

Barinka C, Šácha P, Sklenář J, Man P, Bezouška K, Slusher B S et al. (2004). Identification of the N-glycosylation sites on glutamate carboxypeptidase II necessary for proteolytic activity. Protein Sci 13:1627-1635.

Bařinka C, Rojas C, Slusher B, Pomper M (2012). Glutamate carboxypeptidase II in diagnosis and treatment of neurologic disorders and prostate cancer. Curr Med Chem 19: 856.

Chamberlain P. (2002). Immunogenicity of therapeutic proteins. Part 1: Causes and clinical manifestations of immunogenicity. The Regulatory Review Vol. 5: 4-9.

Cooperberg M R, Broering J M, Carroll P R (2010). Time trends and local variation in primary treatment of localized prostate cancer. J Clin Oncol 28: 1117-1123.

Eiber M, Fendler W P, Rowe S P, Calais J, Hofman M S, Maurer T, Schwarzenboeck S M, Kratowchil C, Herrmann K, Giesel F L. (2017). Prostate-Specific Membrane Antigen Ligands for Imaging and Therapy. J Nucl Med 2017; 58:67S-76S.

Elsässer-Beile U, Wolf P. Gierschner D, Bühler P, Schultze-Seemann W, and Wetterauer U. (2006). A new generation of monoclonal and recombinant antibodies against cell-adherent prostate specific membrane antigen for diagnostic and therapeutic targeting of prostate cancer. The Prostate 66:1359-1370.

Evans J C, Malhotra M, Cryan J F and O'Driscoll C M. (2016). The therapeutic and diagnostic potential of the prostate specific membrane antigen/glutamate carboxypeptidase II (PSMA/GCPII) in cancer and neurological disease. British Journal of Pharmacology 173: 3041-3079.

Foote J and Winter G. (1992). Antibody framework residues affecting the conformation of hypervariable loops. J. Mol. Biol. 224:487-499.

Haffner M C, Kronberger I E, Ross J S, Sheehan C E, Zitt M, Münlmann G et al. (2009). Prostate-specific membrane antigen expression in the neovasculature of gastric and colorectal cancers. Hum Pathol 40:1754-1761.

Horoszewicz J S, Kawinski E, Murphy G. (1986). Monoclonal antibodies to a new antigenic marker in epithelial prostatic cells and serum of prostatic cancer patients. Anticancer Res 7: 927-935.

Israeli R S, Powell C T, Fair W R, Heston W D. (1993). Molecular cloning of a complementary DNA encoding a prostate-specific membrane antigen. Cancer Res 53: 227-230.

Liu H, Moy P, Kim S, Xia Y, Rajasekaran A, Navarro V, Knudsen B, and Bander N H. (1997). Monoclonal antibodies to the extracellular domain of prostate-specific membrane antigen also react with tumor vascular endothelium. Cancer Research 57, 3629-3634.

Nanus D M, Milowsky M I, Kostakoglu L, Smith-Jones P M, Vallabahajosula S, Goldsmith S J, and Bander N H. (2003). Clinical use of monoclonal antibody HuJ591 therapy: targeting prostate specific membrane antigen. Journal of Urology Vol. 170: S84-S89.

Navrátil M, Ptáček J, Šácha P, Starková J, Lubkowski J, Bařinka C et al. (2014). Structural and biochemical characterization of the folyl-poly-γ-1-glutamate hydrolyzing activity of human glutamate carboxypeptidase II. FEBS J 281: 3228-3242.

Queen C. et al. (1989). A humanized antibody that binds to the interleukin 2 receptor. Proc. Natl. Acad. Sci. 86:10029-10033.

Schellekens, H (2002). Immunogenicity of therapeutic proteins: clinical implications and future prospects. Clin. Ther. Vol. 4: 1720-40.

Troyer J, Feng Q, Beckett M, Wright G J. (1995). Biochemical characterization and mapping of the 7 E11-05.3 epitope of the prostate specific membrane antigen. Urol Oncol 1(1):29-37.

Tykvart J, Navratil V, Sedlák F, Corey E, Colombatti M, Fracasso G, Koukolik F, Bárinka C, Sácha P, and Konvalinka J. (2014). Comparative analysis of monoclonal antibodies against prostate-specific membrane antigen (PSMA). The Prostate 1-14.

Wolf P, Freudenberg N, Baler P, Alt K, Schultze-Seemann W, Wetterauer U, and Elsässer-Beile U. (2010a). Three conformational antibodies specific for different PSMA epitopes are promising diagnostic and therapeutic tools for prostate cancer. The Prostate 70:562-569.

Wolf P, Alt K, Wetterauer D, Baler P, Gierschner D, Katzenwadel A, Wetterauer U, and Elsässer-Beile U. (2010b). Preclinical evaluation of a recombinant anti-prostate specific membrane antigen single-chain immunotoxin against prostate cancer. J Immunother. 33:262-271.

Sequences

The following sequences form part of the disclosure of the present application. A WIPO ST 25 compatible electronic sequence listing is provided with this application, too. For the avoidance of doubt, if discrepancies exist between the sequences in the following table and the electronic sequence listing, the sequences in this table shall be deemed to be the correct ones.

h/d, humanized/deimmunized; CDR, complementarity-determining region; FR, framework region; CR, constant region

| SEQ ID No. | Sequence | Description |
| --- | --- | --- |
| SEQ ID No. 1 | GYTFTYF | 3F11-VH-1 CDR H1 |
| SEQ ID No. 2 | GISPGDGNTNYNENFKG | 3F11-VH-1 CDR H2 |
| SEQ ID No. 3 | DGNFPYYAMDS | 3F11-VH-1 CDR H3 |
| SEQ ID No. 4 | RSSQSLVHSNGNTYLH | 3F11-VL-1 CDR L1 |
| SEQ ID No. 5 | TVSNRFS | 3F11-VL-1 CDR L2 |
| SEQ ID No. 6 | SQSTHVPT | 3F11-VL-1 CDR L3 |
| SEQ ID No. 7 | GISPGDGNTNYAQKFQG | 3F11-VH-2 CDR H2 |
| SEQ ID No. 8 | RSSQSLVHSNGQTYLH | 3F11-VL-2 CDR L1 |
| SEQ ID No. 9 | GISPGDGNVNYAQKFQG | 3F11-VH-3 CDR H2 |
| SEQ ID No. 10 | RSSQSLVHSSGQTYLH | 3F11-VL-3 CDR L1 |
| SEQ ID No. 11 | GISPGDSNVNYAQKFQG | 3F11-VH-4 CDR H2 |
| SEQ ID No. 12 | TVSNRAS | 3F11-VL-4 CDR L2 |
| SEQ ID No. 13 | QVQLVQSGAEVKKPGASVKVSCKAS GYTFTYFDINWLRQAPGQGLEWMGG ISPGDGNTNYNENFKGRVTLTIDKSTS TAYMELSSLRSEDTAVYFCARDGNFP YYAMDSWGQGTLVTVSS | 3F11-VH-1, h/d FR |
| SEQ ID No. 14 | DIVMTQSPLSLPVTPGEPASISCRSSQS LVHSNGNTYLHWFLQKPGQSPQLLIY TVSNRFSGVPDRFSGSGSGTDFTLKIS RVEAEDVGVYFCSQSTHVPTFGGGTK VEIKR | 3F11-VL-1, h/d FR |

| SEQ ID No. | Sequence | Description |
| --- | --- | --- |
| SEQ ID No. 15 | QVQLVQSGAEVKKPGASVKVSCKAS GYTFTYFDINWLRQAPGQGLEWMGG ISPGDGNTNYAQKFQGRVTLTIDTSTS TAYMELSSLRSEDTAVYYCARDGNFP YYAMDSWGQGTLVTVSS | 3F11-VH-2, h/d FR |
| SEQ ID No. 16 | DIVMTQSPLSLPVTPGEPASISCRSSQS LVHSNGQTYLHWYLQKPGQSPQLLIY TVSNRFSGVPDRFSGSGSGTDFTLKIS RVEAEDVGVYYCSQSTHVPTFGGGTK VEIKR | 3F11-VL-2, h/d FR |
| SEQ ID No. 17 | QVQLVQSGAEVKKPGASVKVSCKAS GYTFTYFDINWLRQAPGQGLEWMGG ISPGDGNVNYAQKFQGRVTLTIDTSTS TAYMELSSLRSEDTAVYYCARDGNFP YYAMDSWGQGTLVTVSS | 3F11-VH-3, h/d FR |
| SEQ ID No. 18 | DIVMTQSPLSLPVTPGEPASISCRSSQS LVHSSGQTYLHWYLQKPGQSPQLLIY TVSNRFSGVPDRFSGSGSGTDFTLKIS RVEAEDVGVYYCSQSTHVPTFGGGTK VEIKR | 3F11-VL-3, h/d FR |
| SEQ ID No. 19 | QVQLVQSGAEVKKPGASVKVSCKAS GYTFTYFDINWLRQAPGQGLEWMGG ISPGDSNVNYAQKFQGRVTLTIDTSTS TAYMELSSLRSEDTAVYYCARDGNFP YYAMDSWGQGTLVTVSS | 3F11-VH-4, h/d FR |
| SEQ ID No. 20 | DIVMTQSPLSLPVTPGEPASISCRSSQS LVHSSGQTYLHWYQQKPGQSPQLLIY TVSNRASGVPDRFSGSGSGTDFTLKIS RVEAEDVGTYYCSQSTHVPTFGGGTK VEIKR | 3F11-VL-4, h/d FR |
| SEQ ID No. 21 | QVQLVQSGAEVKKPGASVKVSCKAS GYTFTYFDINWLRQAPGQGLEWMGG ISPGDGNTNYNENFKGRVTLTIDKSTS TAYMELSSLRSEDTAVYFCARDGNFP YYAMDSWGQGTLVTVSS ASTKGPSVFPLAPSSKSTSGGTAALG CLVKDYFPEPVTVSWNSGALTSGVH TFPAVLQSSGLYSLSSVVTVPSSSLGT QTYICNVNHKPSNTKVDKKVEPKSC DKTHTCPPCPAPELLGGPSVFLFPPKP KDTLMISRTPEVTCVVVDVSHEDPEV KFNWYVDGVEVHNAKTKPREEQYN STYRVVSVLTVLHQDWLNGKEYKCK VSNKALPAPIEKTISKAKGQPREPQVY TLPPSREEMTKNQVSLTCLVKGFYPS DIAVEWESNGQPENNYKTTPPVLDSD GSFFLYSKLTVDKSRWQQGNVFSCSV MHEALHNHYTQKSLSLSPGK | 3F11-VH-1-CH, h/d FR, h CR |
| SEQ ID No. 22 | DIVMTQSPLSLPVTPGEPASISCRSSQS LVHSNGNTYLHWFLQKPGQSPQLLIY TVSNRFSGVPDRFSGSGSGTDFTLKIS RVEAEDVGVYFCSQSTHVPTFGGGTK VEIKR TVAAPSVFIFPPSDEQLKSGTASVVC LLNNFYPREAKVQWKVDNALQSGN SQESVTEQDSKDSTYSLSSTLTLSKA DYEKHKVYACEVTHQGLSSPVTKSF NRGEC | 3F11-VL-1-CL, h/d FR, h CR |
| SEQ ID No. 23 | QVQLVQSGAEVKKPGASVKVSCKAS GYTFTYFDINWLRQAPGQGLEWMGG ISPGDGNTNYAQKFQGRVTLTIDTSTS TAYMELSSLRSEDTAVYYCARDGNFP YYAMDSWGQGTLVTVSS ASTKGPSVFPLAPSSKSTSGGTAALG CLVKDYFPEPVTVSWNSGALTSGVH TFPAVLQSSGLYSLSSVVTVPSSSLGT QTYICNVNHKPSNTKVDKKVEPKSC DKTHTCPPCPAPELLGGPSVFLFPPKP KDTLMISRTPEVTCVVVDVSHEDPEV | 3F11-VH-2-CH, h/d FR, h CR |

-continued

| SEQ ID No. | Sequence | Description |
|---|---|---|
| | KFNWYVDGVEVHNAKTKPREEQYN STYRVVSVLTVLHQDWLNGKEYKCK VSNKALPAPIEKTISKAKGQPREPQVY TLPPSREEMTKNQVSLTCLVKGFYPS DIAVEWESNGQPENNYKTTPPVLDSD GSFFLYSKLTVDKSRWQQGNVFSCSV MHEALHNHYTQKSLSLSPGK | |
| SEQ ID No. 24 | DIVMTQSPLSLPVTPGEPASISCRSSQS LVHSNGQTYLHWYLQKPGQSPQLLIY TVSNRFSGVPDRFSGSGSGTDFTLKIS RVEAEDVGVYYCSQSTHVPTFGGGTK VEIKR TVAAPSVFIFPPSDEQLKSGTASVVC LLNNFYPREAKVQWKVDNALQSGN SQESVTEQDSKDSTYSLSSTLTLSKA DYEKHKVYACEVTHQGLSSPVTKSF NRGEC | 3F11-VL-2-CL, h/d FR, h CR |
| SEQ ID No. 25 | QVQLVQSGAEVKKPGASVKVSCKAS GYTFTYFDINWLRQAPGQGLEWMGG ISPGDGNVNYAQKFQGRVTLTIDTSTS TAYMELSSLRSEDTAVYYCARDGNFP YYAMDSWGQGTLVTVSS ASTKGPSVFPLAPSSKSTSGGTAALG CLVKDYFPEPVTVSWNSGALTSGVH TFPAVLQSSGLYSLSSVVTVPSSSLGT QTYICNVNHKPSNTKVDKKVEPKSC DKTHTCPPCPAPELLGGPSVFLFPPKP KDTLMISRTPEVTCVVVDVSHEDPEV KFNWYVDGVEVHNAKTKPREEQYN STYRVVSVLTVLHQDWLNGKEYKCK VSNKALPAPIEKTISKAKGQPREPQVY TLPPSREEMTKNQVSLTCLVKGFYPS DIAVEWESNGQPENNYKTTPPVLDSD GSFFLYSKLTVDKSRWQQGNVFSCSV MHEALHNHYTQKSLSLSPGK | 3F11-VH-3-CH, h/d FR, h CR |
| SEQ ID No. 26 | DIVMTQSPLSLPVTPGEPASISCRSSQS LVHSSGQTYLHWYLQKPGQSPQLLIY TVSNRFSGVPDRFSGSGSGTDFTLKIS RVEAEDVGVYYCSQSTHVPTFGGGTK VEIKR TVAAPSVFIFPPSDEQLKSGTASVVC LLNNFYPREAKVQWKVDNALQSGN SQESVTEQDSKDSTYSLSSTLTLSKA DYEKHKVYACEVTHQGLSSPVTKSF NRGEC | 3F11-VL-3-CL, h/d FR, h CR |
| SEQ ID No. 27 | QVQLVQSGAEVKKPGASVKVSCKAS GYTFTYFDINWLRQAPGQGLEWMGG ISPGDSNVNYAQKFQGRVTLTIDTSTS TAYMELSSLRSEDTAVYYCARDGNFP YYAMDSWGQGTLVTVSS ASTKGPSVFPLAPSSKSTSGGTAALG CLVKDYFPEPVTVSWNSGALTSGVH TFPAVLQSSGLYSLSSVVTVPSSSLGT QTYICNVNHKPSNTKVDKKVEPKSC DKTHTCPPCPAPELLGGPSVFLFPPKP KDTLMISRTPEVTCVVVDVSHEDPEV KFNWYVDGVEVHNAKTKPREEQYN STYRVVSVLTVLHQDWLNGKEYKCK VSNKALPAPIEKTISKAKGQPREPQVY TLPPSREEMTKNQVSLTCLVKGFYPS DIAVEWESNGQPENNYKTTPPVLDSD GSFFLYSKLTVDKSRWQQGNVFSCSV MHEALHNHYTQKSLSLSPGK | 3F11-VH-4-CH, h/d FR, h CR |
| SEQ ID No. 28 | DIVMTQSPLSLPVTPGEPASISCRSSQS LVHSSGQTYLHWYQQKPGQSPQLLIY TVSNRASGVPDRFSGSGSGTDFTLKIS RVEAEDVGTYYCSQSTHVPTFGGGTK VEIKR | 3F11-VL-4-CL, h/d FR, h CR |

| SEQ ID No. | Sequence | Description |
|---|---|---|
| | TVAAPSVFIFPPSDEQLKSGTASVVC<br>LLNNFYPREAKVQWKVDNALQSGN<br>SQESVTEQDSKDSTYSLSSTLTLSKA<br>DYEKHKVYACEVTHQGLSSPVTKSF<br>NRGEC | |
| SEQ ID No. 29 | ASTKGPSVFPLAPSSKSTSGGTAALG<br>CLVKDYFPEPVTVSWNSGALTSGVH<br>TFPAVLQSSGLYSLSSVVTVPSSSLGT<br>QTYICNVNHKPSNTKVDKKVEPKSC<br>DKTHTCPPCPAPELLGGPSVFLFPPKP<br>KDTLMISRTPEVTCVVVDVSHEDPEV<br>KFNWYVDGVEVHNAKTKPREEQYN<br>STYRVVSVLTVLHQDWLNGKEYKCK<br>VSNKALPAPIEKTISKAKGQPREPQVY<br>TLPPSREEMTKNQVSLTCLVKGFYPS<br>DIAVEWESNGQPENNYKTTPPVLDSD<br>GSFFLYSKLTVDKSRWQQGNVFSCSV<br>MHEALHNHYTQKSLSLSPGK | H-CR (hIgG1 CH1 CH2 CH3) |
| SEQ ID No. 30 | TVAAPSVFIFPPSDEQLKSGTASVVC<br>LLNNFYPREAKVQWKVDNALQSGN<br>SQESVTEQDSKDSTYSLSSTLTLSKA<br>DYEKHKVYACEVTHQGLSSPVTKSF<br>NRGEC | L-CR (hIgG1 CL1) |
| SEQ ID No. 31 | MAQVQLQQSGAELVEPGASVKLSC<br>KASGYTFTYFDINWLRQRPEQGLEW<br>IGGISPGDGNTNYNENFKGKATLTID<br>KSSTTAYIQLSRLTSEDSAVYFCARD<br>GNFPYYAMDSWGQGTSVTVSSAKT<br>TPKLEEGEFSEARVDIELTQSPLSLPV<br>ILGDQASISCRSSQSLVHSNGNTYLH<br>WFLQKPGQSPKLLIYTVSNRFSGVPD<br>RFSGSGSGTDFTLKISRVEAEDLGVY<br>FCSQSTHVPTFGGGTKLEIKRADAAA<br>AGS | scFv D7<br>(Ntag-VH-Linker-VL-Ctag) |
| SEQ ID No. 32 | $GX_1TX_2TX_3X_4$ | CDR H1, wherein $X_1$, $X_2$, $X_3$ and $X_4$ each are Y, F, W, |
| SEQ ID No. 33 | $GISPGDX_5NX_6NYX_7X_8X_9FX_{10}G$ | CDR H2, wherein $X_5$ is G, S; $X_6$ is T, V; $X_7$ is N, A; $X_8$ is E, Q; $X_9$ is N, K; $X_{10}$ is K, Q; |
| SEQ ID No. 34 | $DGNX_{11}PX_{12}X_{13}AMDS$ | CDR H3, wherein $X_{11}$, $X_{12}$, $X_{13}$ each are Y, F, W. |
| SEQ ID No. 35 | $RSSQSLVHSX_1GX_2TX_3LH$ | CDR L1, wherein $X_1$ is N, S; $X_2$ is N, Q; $X_3$ is Y, F, W |
| SEQ ID No. 36 | $TVSNRX_4S$ | CDR L2, wherein $X_4$ is A, Y, F, W |
| SEQ ID No. 37 | SQSTHVPT | CDR L3 |

What is claimed is:

1. A humanized antibody, or antigen-binding fragment or antigen-binding portion thereof, comprising a variable heavy (VH) domain comprising
a CDR H1 sequence according to SEQ ID No. 1,
a CDR H2 sequence selected from any of the sequences according to SEQ ID No. 2, SEQ ID No. 7, SEQ ID No. 9, and SEQ ID No. 11,
a CDR H3 sequence according to SEQ ID No. 3,
and a variable light (VL) domain comprising
a CDR L1 sequence selected from any of the sequences according to SEQ ID No. 4, SEQ ID No. 8, and SEQ ID No. 10,
a CDR L2 sequence selected from any of the sequences according to SEQ ID No. 5 and SEQ ID No. 12, and
a CDR L3 sequence according to SEQ ID No. 6,
but not comprising the combination of a CDR H1 sequence according to SEQ ID No. 1, a CDR H2 sequence according to SEQ ID No. 2 or 7, a CDR H3 sequence according to SEQ ID No. 3, a CDR L1 sequence according to SEQ ID No. 4, a CDR L2 sequence according to SEQ ID No. 5, and a CDR L3 sequence according to SEQ ID 6,
that binds to the extracellular domain of prostate specific membrane antigen (PSMA).

2. The humanized antibody, or antigen-binding fragment or antigen-binding portion thereof, according to claim 1, comprising a VH domain having at least 90% sequence homology to a sequence selected from any of the sequences according to SEQ ID No. 13, SEQ ID No. 15, SEQ ID No. 17, and SEQ ID No. 19.

3. The humanized antibody, or antigen-binding fragment or antigen-binding portion thereof, according to claim 1, comprising a VH domain sequence selected from any of the sequences according to SEQ ID No. 13, SEQ ID No. 15, SEQ ID No. 17, and SEQ ID No. 19.

4. The humanized antibody, or antigen-binding fragment or antigen-binding portion thereof, according to claim 1, comprising a VL domain having at least 90% sequence homology to a sequence selected from any of the sequences according to SEQ ID No. 14, SEQ ID No. 16, SEQ ID No. 18, and SEQ ID No. 20.

5. The humanized antibody, or antigen-binding fragment or antigen-binding portion thereof, according to claim 1, comprising a VL domain sequence selected from any of the sequences according to SEQ ID No. 14, SEQ ID No. 16, SEQ ID No. 18, and SEQ ID No. 20.

6. The humanized antibody, or antigen-binding fragment or antigen-binding portion thereof, according to claim 1 comprising
- the VH domain sequence according to SEQ ID No. 13 and a VL domain sequence selected from any of the sequences according to SEQ ID No. 14, SEQ ID No. 16, SEQ ID No. 18, and SEQ ID No. 20, or
- the VH domain sequence according to SEQ ID No. 15 and a VL domain sequence selected from any of the sequences according to SEQ ID No. 14, SEQ ID No. 16, SEQ ID No. 18, and SEQ ID No. 20, or
- the VH domain sequence according to SEQ ID No. 17 and a VL domain sequence selected from any of the sequences according to SEQ ID No. 14, SEQ ID No. 16, SEQ ID No. 18, and SEQ ID No. 20, or
- the VH domain sequence according to SEQ ID No. 19 and a VL domain sequence selected from any of the sequences according to SEQ ID No. 14, SEQ ID No. 16, SEQ ID No. 18, and SEQ ID No. 20.

7. The humanized antibody, or antigen-binding fragment or antigen-binding portion thereof, according to claim 3, comprising at least one heavy chain comprising any of the sequences SEQ ID No. 21, SEQ ID No. 23, SEQ ID No. 25, or SEQ ID No. 27.

8. The humanized antibody, or antigen-binding fragment or antigen-binding portion thereof, according to claim 5, comprising at least one light chain comprising any of the sequences SEQ ID No. 22, SEQ ID No. 24, SEQ ID No. 26, or SEQ ID No. 28.

9. A humanized antibody, or antigen-binding fragment or antigen-binding portion thereof, comprising at least one heavy chain comprising any of the sequences SEQ ID Nos. 21, 23, 25 or 27, and at least one light chain comprising any of the sequences SEQ ID Nos. 22, 24, 26 or 28.

10. A humanized antibody, or antigen-binding fragment or antigen-binding portion thereof, comprising at least one heavy chain comprising SEQ ID No. 27 and at least one light chain comprising SEQ ID No. 28.

11. The humanized antibody, or antigen-binding fragment or antigen-binding portion thereof, according to claim 1, binding to the extracellular domain of PSMA with an affinity of EC50<0.4 µg/ml.

12. The humanized antibody, or antigen-binding fragment or antigen-binding portion thereof, according to claim 1, wherein the antibody is glycosylated.

13. The humanized antibody, or antigen-binding fragment or antigen-binding portion thereof, according to claim 12, further comprising a heavy chain constant region (H—CR) sequence according to SEQ ID No. 29 and an N-linked oligosaccharide chain at asparagine 297 of the heavy chain.

14. The humanized antibody, or antigen-binding fragment or antigen-binding portion thereof, according to claim 1, wherein the antibody is of isotype IgG.

15. A humanized antigen-binding fragment according to claim 1, wherein the antibody fragment is selected from the group consisting of a variable domain (Fv), a Fab fragment, an F(ab)2 fragment, and a single-chain Fv (scFv).

16. An antibody-drug conjugate (ADC) comprising the humanized antibody, or an antigen-binding fragment or antigen-binding portion thereof, according to claim 1, conjugated to a therapeutic agent, optionally via a linker moiety.

17. A pharmaceutical formulation comprising a humanized antibody, or antigen-binding fragment or antigen-binding portion thereof, according to claim 1, together with at least a pharmaceutically acceptable carrier.

18. A method of treating a patient suffering from prostate cancer comprising administering an effective amount of a humanized antibody, or antigen-binding fragment or antigen-binding portion thereof, according to claim 1 to the patient.

19. A nucleic acid encoding for a humanized antibody, an antigen-binding fragment or antigen-binding portion thereof, according to claim 1.

20. A host cell capable of producing a humanized antibody, an antigen-binding fragment or antigen-binding portion thereof, according to claim 1.

* * * * *

SEQUENCE LISTING

<160> NUMBER OF SEQ ID NOS: 37

<210> SEQ ID NO 1
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 1

Gly Tyr Thr Phe Thr Tyr Phe
1               5

```
<210> SEQ ID NO 2
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 2

Gly Ile Ser Pro Gly Asp Gly Asn Thr Asn Tyr Asn Glu Asn Phe Lys
1               5                   10                  15
Gly

<210> SEQ ID NO 3
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 3

Asp Gly Asn Phe Pro Tyr Tyr Ala Met Asp Ser
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 4

Arg Ser Ser Gln Ser Leu Val His Ser Asn Gly Asn Thr Tyr Leu His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 5

Thr Val Ser Asn Arg Phe Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 6

Ser Gln Ser Thr His Val Pro Thr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 7

Gly Ile Ser Pro Gly Asp Gly Asn Thr Asn Tyr Ala Gln Lys Phe Gln
1               5                   10                  15
```

Gly

<210> SEQ ID NO 8
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 8

Arg Ser Ser Gln Ser Leu Val His Ser Asn Gly Gln Thr Tyr Leu His
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 9

Gly Ile Ser Pro Gly Asp Gly Asn Val Asn Tyr Ala Gln Lys Phe Gln
1               5                   10                  15

Gly

<210> SEQ ID NO 10
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 10

Arg Ser Ser Gln Ser Leu Val His Ser Ser Gly Gln Thr Tyr Leu His
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 11

Gly Ile Ser Pro Gly Asp Ser Asn Val Asn Tyr Ala Gln Lys Phe Gln
1               5                   10                  15

Gly

<210> SEQ ID NO 12
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 12

Thr Val Ser Asn Arg Ala Ser
1               5

<210> SEQ ID NO 13
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
            20                  25                  30

Asp Ile Asn Trp Leu Arg Gln Ala Pro Gly Gln Gly Leu Glu Trp Met
        35                  40                  45

Gly Gly Ile Ser Pro Gly Asp Gly Asn Thr Asn Tyr Asn Glu Asn Phe
    50                  55                  60

Lys Gly Arg Val Thr Leu Thr Ile Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Asn Phe Pro Tyr Tyr Ala Met Asp Ser Trp Gly Gln
            100                 105                 110

Gly Thr Leu Val Thr Val Ser Ser
            115                 120

<210> SEQ ID NO 14
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 14

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Phe Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Thr Phe Gly Gly Gly Thr Lys Val Glu Ile Lys Arg
            100                 105                 110

<210> SEQ ID NO 15
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
            20                  25                  30

Asp Ile Asn Trp Leu Arg Gln Ala Pro Gly Gln Gly Leu Glu Trp Met
        35                  40                  45

Gly Gly Ile Ser Pro Gly Asp Gly Asn Thr Asn Tyr Ala Gln Lys Phe
    50                  55                  60

Gln Gly Arg Val Thr Leu Thr Ile Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Phe Pro Tyr Tyr Ala Met Asp Ser Trp Gly Gln
            100                 105                 110

Gly Thr Leu Val Thr Val Ser Ser
        115                 120

<210> SEQ ID NO 16
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 16

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Gln Thr Tyr Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Thr Phe Gly Gly Gly Thr Lys Val Glu Ile Lys Arg
            100                 105                 110

<210> SEQ ID NO 17
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
            20                  25                  30

Asp Ile Asn Trp Leu Arg Gln Ala Pro Gly Gln Gly Leu Glu Trp Met
        35                  40                  45

Gly Gly Ile Ser Pro Gly Asp Gly Asn Val Asn Tyr Ala Gln Lys Phe
    50                  55                  60

Gln Gly Arg Val Thr Leu Thr Ile Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Phe Pro Tyr Tyr Ala Met Asp Ser Trp Gly Gln
            100                 105                 110

Gly Thr Leu Val Thr Val Ser Ser
        115                 120

<210> SEQ ID NO 18

<211> LENGTH: 112
<212> TYPE: PRT
<213> ORGANISM: Artificial Sequence
<220> FEATURE:
<223> OTHER INFORMATION: Synthetic Sequence

<400> SEQUENCE: 18

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Ser Gly Gln Thr Tyr Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Thr Phe Gly Gly Gly Thr Lys Val Glu Ile Lys Arg
            100                 105                 110

<210> SEQ ID NO 19
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
            20                  25                  30

Asp Ile Asn Trp Leu Arg Gln Ala Pro Gly Gln Gly Leu Glu Trp Met
        35                  40                  45

Gly Gly Ile Ser Pro Gly Asp Ser Asn Val Asn Tyr Ala Gln Lys Phe
    50                  55                  60

Gln Gly Arg Val Thr Leu Thr Ile Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Phe Pro Tyr Tyr Ala Met Asp Ser Trp Gly Gln
            100                 105                 110

Gly Thr Leu Val Thr Val Ser Ser
        115                 120

<210> SEQ ID NO 20
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 20

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

```
Ser Gly Gln Thr Tyr Leu His Trp Tyr Gln Gln Lys Pro Gly Gln Ser
            35                  40                  45

Pro Gln Leu Leu Ile Tyr Thr Val Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Thr Tyr Tyr Cys Ser Gln Ser
                85                  90                  95

Thr His Val Pro Thr Phe Gly Gly Gly Thr Lys Val Glu Ile Lys Arg
                100                 105                 110
```

<210> SEQ ID NO 21
<211> LENGTH: 450
<212> TYPE: PRT
<213> ORGANISM: Artificial Sequence
<220> FEATURE:
<223> OTHER INFORMATION: Synthetic Sequence

<400> SEQUENCE: 21

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Tyr Phe
            20                  25                  30

Asp Ile Asn Trp Leu Arg Gln Ala Pro Gly Gln Gly Leu Glu Trp Met
        35                  40                  45

Gly Gly Ile Ser Pro Gly Asp Gly Asn Thr Asn Tyr Asn Glu Asn Phe
    50                  55                  60

Lys Gly Arg Val Thr Leu Thr Ile Asp Lys Ser Thr Ser Thr Ala Tyr
 65                  70                  75                  80

Met Glu Leu Ser Ser Leu Arg Ser Glu Asp Thr Ala Val Tyr Phe Cys
                85                  90                  95

Ala Arg Asp Gly Asn Phe Pro Tyr Tyr Ala Met Asp Ser Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 22
<211> LENGTH: 218
<212> TYPE: PRT
<213> ORGANISM: Artificial Sequence
<220> FEATURE:
<223> OTHER INFORMATION: Synthetic Sequence

<400> SEQUENCE: 22

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Phe Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 23
<211> LENGTH: 450
<212> TYPE: PRT
<213> ORGANISM: Artificial Sequence
<220> FEATURE:
<223> OTHER INFORMATION: Synthetic Sequence

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
            20                  25                  30

Asp Ile Asn Trp Leu Arg Gln Ala Pro Gly Gln Gly Leu Glu Trp Met
        35                  40                  45

Gly Gly Ile Ser Pro Gly Asp Gly Asn Thr Asn Tyr Ala Gln Lys Phe
    50                  55                  60

Gln Gly Arg Val Thr Leu Thr Ile Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Phe Pro Tyr Tyr Ala Met Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 24
<211> LENGTH: 218
<212> TYPE: PRT
<213> ORGANISM: Artificial Sequence
<220> FEATURE:
<223> OTHER INFORMATION: Synthetic Sequence

<400> SEQUENCE: 24

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Gln Thr Tyr Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 25
<211> LENGTH: 450
```

```
<212> TYPE: PRT
<213> ORGANISM: Artificial Sequence
<220> FEATURE:
<223> OTHER INFORMATION: Synthetic Sequence

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
            20                  25                  30

Asp Ile Asn Trp Leu Arg Gln Ala Pro Gly Gln Gly Leu Glu Trp Met
        35                  40                  45

Gly Gly Ile Ser Pro Gly Asp Gly Asn Val Asn Tyr Ala Gln Lys Phe
50                  55                  60

Gln Gly Arg Val Thr Leu Thr Ile Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Phe Pro Tyr Tyr Ala Met Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 26
<211> LENGTH: 218
<212> TYPE: PRT
<213> ORGANISM: Artificial Sequence
<220> FEATURE:
<223> OTHER INFORMATION: Synthetic Sequence

<400> SEQUENCE: 26

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Ser Gly Gln Thr Tyr Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 27
<211> LENGTH: 450
<212> TYPE: PRT
<213> ORGANISM: Artificial Sequence
<220> FEATURE:
<223> OTHER INFORMATION: Synthetic Sequence

<400> SEQUENCE: 27

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Tyr Phe
             20                  25                  30

Asp Ile Asn Trp Leu Arg Gln Ala Pro Gly Gln Gly Leu Glu Trp Met
         35                  40                  45

Gly Gly Ile Ser Pro Gly Asp Ser Asn Val Asn Tyr Ala Gln Lys Phe
 50                  55                  60

Gln Gly Arg Val Thr Leu Thr Ile Asp Thr Ser Thr Ser Thr Ala Tyr
65                   70                  75                  80

Met Glu Leu Ser Ser Leu Arg Ser Glu Asp Thr Ala Val Tyr Tyr Cys
                 85                  90                  95

Ala Arg Asp Gly Asn Phe Pro Tyr Tyr Ala Met Asp Ser Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
         355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430
```

Glu Ala Leu His Asn His Tyr Thr Gln Lys Ser Leu Ser Leu Ser Pro
            435                 440                 445

Gly Lys
    450

<210> SEQ ID NO 28
<211> LENGTH: 218
<212> TYPE: PRT
<213> ORGANISM: Artificial Sequence
<220> FEATURE:
<223> OTHER INFORMATION: Synthetic Sequence

<400> SEQUENCE: 28

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Ser Gly Gln Thr Tyr Leu His Trp Tyr Gln Gln Lys Pro Gly Gln Ser
        35                  40                  45

Pro Gln Leu Leu Ile Tyr Thr Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Thr Tyr Tyr Cys Ser Gln Ser
                85                  90                  95

Thr His Val Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 29
<211> LENGTH: 330
<212> TYPE: PRT
<213> ORGANISM: Artificial Sequence
<220> FEATURE:
<223> OTHER INFORMATION: Synthetic Sequence

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270    Asn

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 30
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 30

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

```
Val Thr Lys Ser Phe Asn Arg Gly Glu Cys
            100                 105

<210> SEQ ID NO 31
<211> LENGTH: 259
<212> TYPE: PRT
<213> ORGANISM: Artificial Sequence
<220> FEATURE:
<223> OTHER INFORMATION: Synthetic Sequence

<400> SEQUENCE: 31

Met Ala Gln Val Gln Leu Gln Gln Ser Gly Ala Glu Leu Val Glu Pro
1               5                   10                  15

Gly Ala Ser Val Lys Leu Ser Cys Lys Ala Ser Gly Tyr Thr Phe Thr
            20                  25                  30

Tyr Phe Asp Ile Asn Trp Leu Arg Gln Arg Pro Glu Gln Gly Leu Glu
        35                  40                  45

Trp Ile Gly Gly Ile Ser Pro Gly Asp Gly Asn Thr Asn Tyr Asn Glu
    50                  55                  60

Asn Phe Lys Gly Lys Ala Thr Leu Thr Ile Asp Lys Ser Ser Thr Thr
65                  70                  75                  80

Ala Tyr Ile Gln Leu Ser Arg Leu Thr Ser Glu Asp Ser Ala Val Tyr
                85                  90                  95

Phe Cys Ala Arg Asp Gly Asn Phe Pro Tyr Tyr Ala Met Asp Ser Trp
            100                 105                 110

Gly Gln Gly Thr Ser Val Thr Val Ser Ser Ala Lys Thr Thr Pro Lys
        115                 120                 125

Leu Glu Glu Gly Glu Phe Ser Glu Ala Arg Val Asp Ile Glu Leu Thr
    130                 135                 140

Gln Ser Pro Leu Ser Leu Pro Val Ile Leu Gly Asp Gln Ala Ser Ile
145                 150                 155                 160

Ser Cys Arg Ser Ser Gln Ser Leu Val His Ser Asn Gly Asn Thr Tyr
                165                 170                 175

Leu His Trp Phe Leu Gln Lys Pro Gly Gln Ser Pro Lys Leu Leu Ile
            180                 185                 190

Tyr Thr Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Leu Gly Val Tyr Phe Cys Ser Gln Ser Thr His Val Pro Thr
225                 230                 235                 240

Phe Gly Gly Gly Thr Lys Leu Glu Ile Lys Arg Ala Asp Ala Ala Ala
                245                 250                 255

Ala Gly Ser

<210> SEQ ID NO 32
<211> LENGTH: 7
<212> TYPE: PRT
<213> ORGANISM: Artificial Sequence
<220> FEATURE:
<223> OTHER INFORMATION: Synthetic Sequence
<220> FEATURE:
<221> NAME/KEY: Xaa
<222> LOCATION: (2)..(2)
<223> OTHER INFORMATION: Xaa is Tyrosine, Phenylalanine or Tryptophan
<220> FEATURE:
<221> NAME/KEY: Xaa
<222> LOCATION: (4)..(4)
<223> OTHER INFORMATION: Xaa is Tyrosine, Phenylalanine or Tryptophan
```

```
<220> FEATURE:
<221> NAME/KEY: Xaa
<222> LOCATION: (6)..(6)
<223> OTHER INFORMATION: Xaa is Tyrosine, Phenylalanine or Tryptophan
<220> FEATURE:
<221> NAME/KEY: Xaa
<222> LOCATION: (7)..(7)
<223> OTHER INFORMATION: Xaa is Tyrosine, Phenylalanine or Tryptophan

<400> SEQUENCE: 32

Gly Xaa Thr Xaa Thr Xaa Xaa
1               5

<210> SEQ ID NO 33
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Xaa
<222> LOCATION: (7)..(7)
<223> OTHER INFORMATION: Xaa is Glycine or Serine
<220> FEATURE:
<221> NAME/KEY: Xaa
<222> LOCATION: (9)..(9)
<223> OTHER INFORMATION: Xaa is Threonine or Valine
<220> FEATURE:
<221> NAME/KEY: Xaa
<222> LOCATION: (12)..(12)
<223> OTHER INFORMATION: Xaa is Asparagine or Alanine
<220> FEATURE:
<221> NAME/KEY: Xaa
<222> LOCATION: (13)..(13)
<223> OTHER INFORMATION: Xaa is Glutamic acid or Glutamic acid
<220> FEATURE:
<221> NAME/KEY: Xaa
<222> LOCATION: (14)..(14)
<223> OTHER INFORMATION: Xaa is Asparagine or Lysine
<220> FEATURE:
<221> NAME/KEY: Xaa
<222> LOCATION: (16)..(16)
<223> OTHER INFORMATION: Xaa is Lysine or Glutamine

<400> SEQUENCE: 33

Gly Ile Ser Pro Gly Asp Xaa Asn Xaa Asn Tyr Xaa Xaa Xaa Phe Xaa
1               5                   10                  15

Gly

<210> SEQ ID NO 34
<211> LENGTH: 11
<212> TYPE: PRT
<213> ORGANISM: Artificial Sequence
<220> FEATURE:
<223> OTHER INFORMATION: Synthetic Sequence
<220> FEATURE:
<221> NAME/KEY: Xaa
<222> LOCATION: (4)..(4)
<223> OTHER INFORMATION: Xaa is Tyrosine, Phenylalanine or Tryptophan
<220> FEATURE:
<221> NAME/KEY: Xaa
<222> LOCATION: (6)..(6)
<223> OTHER INFORMATION: Xaa is Tyrosine, Phenylalanine or Tryptophan
<220> FEATURE:
<221> NAME/KEY: Xaa
<222> LOCATION: (7)..(7)
<223> OTHER INFORMATION: Xaa is Tyrosine, Phenylalanine or Tryptophan

<400> SEQUENCE: 34

Asp Gly Asn Xaa Pro Xaa Xaa Ala Met Asp Ser
1               5                   10
```

```
<210> SEQ ID NO 35
<211> LENGTH: 16
<212> TYPE: PRT
<213> ORGANISM: Artificial Sequence
<220> FEATURE:
<223> OTHER INFORMATION: Synthetic Sequence
<220> FEATURE:
<221> NAME/KEY: Xaa
<222> LOCATION: (10)..(10)
<223> OTHER INFORMATION: Xaa is Asparagine or Serine
<220> FEATURE:
<221> NAME/KEY: Xaa
<222> LOCATION: (12)..(12)
<223> OTHER INFORMATION: Xaa is Asparagine or Glutamine
<220> FEATURE:
<221> NAME/KEY: Xaa
<222> LOCATION: (14)..(14)
<223> OTHER INFORMATION: Xaa is Tyrosine, Phenylalanine or Tryptophan

<400> SEQUENCE: 35

Arg Ser Ser Gln Ser Leu Val His Ser Xaa Gly Xaa Thr Xaa Leu His
1               5                   10                  15

<210> SEQ ID NO 36
<211> LENGTH: 7
<212> TYPE: PRT
<213> ORGANISM: Artificial Sequence
<220> FEATURE:
<223> OTHER INFORMATION: Synthetic Sequence
<220> FEATURE:
<221> NAME/KEY: Xaa
<222> LOCATION: (6)..(6)
<223> OTHER INFORMATION: Xaa is Alanine, Tyrosine, Phenylalanine or
      Tryptophan

<400> SEQUENCE: 36

Thr Val Ser Asn Arg Xaa Ser
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 37

Ser Gln Ser Thr His Val Pro Thr
1               5
```